(12) United States Patent
Mayaud

(10) Patent No.: US 7,606,723 B2
(45) Date of Patent: Oct. 20, 2009

(54) COMPUTERIZED PRESCRIPTION SYSTEM FOR GATHERING AND PRESENTING INFORMATION RELATING TO PHARMACEUTICALS

(75) Inventor: Christian Mayaud, New Canaan, CT (US)

(73) Assignee: Cybear, L.L.C.

( * ) Notice: Subject to any disclaimer, the term of this patent is extended or adjusted under 35 U.S.C. 154(b) by 831 days.

(21) Appl. No.: 10/918,967

(22) Filed: Aug. 16, 2004

(65) Prior Publication Data

US 2005/0060197 A1 Mar. 17, 2005

Related U.S. Application Data

(63) Continuation of application No. 09/121,596, filed on Jul. 24, 1998, now abandoned, which is a continuation of application No. 08/942,372, filed on Oct. 2, 1997, now Pat. No. 5,845,255, which is a continuation of application No. 08/330,745, filed on Oct. 28, 1994, now abandoned.

(51) Int. Cl.
*G06Q 10/00* (2006.01)

(52) U.S. Cl. .................................. 705/2; 705/3; 600/300

(58) Field of Classification Search .................. 705/2, 705/3; 600/300
See application file for complete search history.

(56) References Cited

U.S. PATENT DOCUMENTS

| 5,070,452 | A | * | 12/1991 | Doyle et al. | 705/2 |
| 5,832,450 | A | * | 11/1998 | Myers et al. | 705/3 |
| 5,833,599 | A | * | 11/1998 | Schrier et al. | 600/300 |
| 5,845,253 | A | * | 12/1998 | Rensimer et al. | 705/2 |
| 5,867,821 | A | * | 2/1999 | Ballantyne et al. | 705/2 |

* cited by examiner

*Primary Examiner*—Robert W Morgan
(74) *Attorney, Agent, or Firm*—Robert M. Schwartz; David W. Barman

(57) ABSTRACT

This invention relates to professional data management systems useful in the production of product specification documents such as prescriptions, service or parts orders, insurance contracts and the like that require detailed product and history information from multiple extensive information sources, especially remote heterogenous sources. More particularly, the invention relates to systems that assist professionals perform their everyday work in specifying customized technical products. A particularly preferred embodiment relates to a computer-implemented prescription management system to assist physicians in prescribing and reviewing drugs.

2 Claims, 16 Drawing Sheets

FIGURE 7

Select Drug — 112

Conditions — 114
- Dx-Personal
- Dx-Alphabetic — 114
- Dx-Category
- Px-Patient — 114
- Dx-Custom 1
- Dx-Custom 2 — 114

Conditions:
- Angina/CAD
- Asthma — 116
- Bronchitis
- CHF
- Contraception
- COPD
- Cystitis
- Depression
- Diabetes — 116
- GERD
- Hypertension
- Hypothyroidism
- Migraine
- Osteoarth
- Otitis Media
- Pneumonia
- Prostatitis
- PUD/G.sutritis
- Rheumatory Arthritis — 116
- Rhinitis
- Sinusitis Formulary Drugs — 110
- Cimetidine
- Ranitidine
- Antacid
- Other Nonformulary Drugs — 124
- Famotidine — 122
- Nazatidine
- Omeprazole
- Sucralfate

| | Select Drugs | | | |
|---|---|---|---|---|
| | Body System | Condition | | Drug |
| Dx by Body System | Cardiovascular | Cancer | analgesics | Advil Pediatric |
| Dx by Alpha | Digestive | Gout | narcotics | Anaprox |
| Rx by Therapeutic Class | EENT | Infections | NSAIDS | Anaprox DS |
| Rx by Alpha | Endocrine | Muscle spasm | salicylates | Butazolidin |
| | General Symptoms | Neuro-muscular disease | | Butazone |
| | Infectious Disease | Osteoarthritis | | Children's Advil |
| | Integument | Osteoporosis / dystrophy | | Children's Motrin |
| | Lymphatic/hematologic | Pain | | Clinoril |
| | Mental Illness | Rheumatoid arthritis | | Diclofenac Potassium |
| | Musculo-skeletal | | | Diclofenac Sodium |
| | Neurologic | | | Feldene |
| | Respiratory | | | Fenofon |
| | Trauma | | | Fenoprofen Calcium |
| | Uro-genital | | | Flurbiprofen |
| | | | | Ibuprofen |
| | | | | Indocin |
| | | | | Indocin SR |
| | | | | Indomethacin |
| | | | | Indomethacin Sodium |
| | | | | Indomethacin SR |
| | | | | Ketoprofen |
| | | | | Ketorolac Trometha |
| | | | | Meclodium |
| | | | | Meclofenamate Sod |
| | | | | Meclomen |
| | | | | Mefenamic Acid |
| | | | | Motrin |
| | | | | Nalfon |

| Drug Category | Drug |
|---|---|
| cough/cold preps | Acetazolamide |
| coumadin | Acetazolamide Sodium |
| cromolyn —119 | Aldactazide 25/25 |
| cycloplegics | Aldactazide 50/50 |
| decongestants | Aldactone —121 |
| digestive aids | Aldarex Plus 25/25 |
| digestive enzymes | Altex |
| digitalis | Amiloride & HCTZ |
| direct muscle relaxant | Amiloride HCl |
| diuretics | Anhydron |
| DMSO | Bendroflumethiazide |
| dopaminergics | Bumetanide |
| ergot alkaloids | Bumex |
| erythromycins | Chlorothizide |
| estrogen comb. | Chlorothiazide Sodium |
| flouride(s) | Chlorthalidone |
| floxacins | Cyclothiazide |
| gastric acidfiers | Daranide |
| glucocorticoids | Diamox —121 |
| gold preps | Diamox Sequets |
| growth hormone | Dichlorphenamide |
| H2-antagonists | Diurul |
| heparin | Diuril |
| hormones —119 | Dyazide —121 |
| hypokalemics | Dyrenium |
| immunosuppressives | Edecrin |
| inhalants | Enduron |
|  | Esidrix |

Dx by Body System —114
Dx by Alpha —114
Dx by Therapeutic Class —115
Rx by Alpha —115
Rx Personal

FIGURE 10

Select Condition - Drug Specified

| Drug List | Drug | Personal | Other |
|---|---|---|---|
| Rx Personal | Achromycin | | Acne |
| Rx-Alphabetic — 115 | Achromycin V | | ADD |
| Rx-Category | Amdinocillin | | Alcohol Abuse — 116 |
| Rx-Custom 1 | Amoxicillin — 121 | | Anemia |
| Rx-Custom 2 | Amoxil | | Angina |
| | Ampicillin | | Anti-toxin/venom |
| | Ampicillin Sodium | | Anxiety disorders |
| | Ampicillin w/Proben | | Arrhythmia |
| | Augmentin — 121 | | Asthma |
| | Azithromycin | | Bacterial — 116 |
| | Azlocillin Sodium | | Bladder disorder |
| | Bactrim | | BPH |
| | Bactrim DS | | Bronchitis |
| | Beepen-VK | | Cancer |
| | Betapen-VK | | CHF |
| | Biaxin | | Chloamphenicol — 116 |
| | Ceclor — 121 | | Cholelithiasis |
| | Cefaclor | | Cirrhosis / Hepatitis |
| | Cefadroxil | Otitis media | Clotting disorders |
| | Cefanex | Konsili's | Constipation |
| | Cefixime | Urinary tract infec — 116 | Contraception |
| | Cefobid | | Convulsive disorders |
| | Cefotan | | COPD |
| | Cefprozil | | Dementia |
| | Ceftin — 121 | | Depression — 116 |
| | Cefzil | | Dermatitis, eczema, se |
| | Cephalexin | | Diabetes / Diabetes Ins |
| | Cephalothin Sodium | | Diarrhea |

US 7,606,723 B2

COMPUTERIZED PRESCRIPTION SYSTEM FOR GATHERING AND PRESENTING INFORMATION RELATING TO PHARMACEUTICALS

CROSS REFERENCE TO RELATED APPLICATIONS

This application is a Continuation of U.S. patent application Ser. No. 09/121,596 filed Jul. 24, 1998 (now abandoned), which is a Continuation of U.S. patent application Ser. No. 08/942,372 filed Oct. 2, 1997 (now U.S. Pat. No. 5,845,255), which is a continuation of U.S. patent application Ser. No. 08/330,745, filed Oct. 28, 1994, now abandoned, the disclosures of which are hereby incorporated by reference in their entirety.

Applicant incorporates herein by reference the heretofore above enumerated prior applications, namely application Ser. No. 09/121,596 (now abandoned) application Ser. No. 08/942,372 (now U.S. Pat. No. 5,845,255) and application Ser. No. 08/330,745 (now abandoned).

TECHNICAL FIELD

This invention relates to professional data management systems useful in the production of product specification documents such as prescriptions, service or parts orders, insurance contracts and the like that require detailed product and history information from multiple extensive information sources, especially remote heterogenous sources. More particularly, the invention relates to systems that assist professionals perform their everyday work in specifying customized technical products. A particularly preferred embodiment relates to a computer-implemented prescription management system to assist physicians in prescribing and reviewing drugs.

BACKGROUND

An important professional activity undertaken by most physicians during the course of their day is the prescribing of drugs. Many physicians prescribe a great number of drugs every day. Studies show that over two thirds of all doctor-patient encounters were completed with the writing of a prescription. In 1993 typical prescribers were prescribing in excess of two hundred thousand dollars-worth of drugs annually. While most physicians exercise the utmost of professional skill and caution in prescribing, there are inherent difficulties and uncertainties in the process. Most physicians will probably agree that they do not have access to adequate, reliable drug information and relevant patient information at the time and point of prescription. In particular, information regarding relevant new drugs, comparative efficacy, and importantly, relative costs, may not be readily and conveniently available to a physician creating a new prescription, as well as relevant patient information such as current conditions being treated, current treatments, and preferred medications for conditions, pursuant to requirements of the patient's drug formulary.

Nevertheless, while accessing it is impractical for the typical practitioner, such information is available to any physician willing to take the time and make the effort to obtain it.

In contrast, integrated patient-specific information which is directly relevant to treatment management for the subject patient is frequently both unavailable to, and unobtainable by, a prescribing physician unless that physician's institution or organization has been exhaustively responsible for the subject patient's prior care and maintains sophisticated computerized records. Information as to allergies, current prescriptions and currently active conditions is clearly desirable or essential for intelligent prescribing. In 1994, few prescribing sessions are conducted with the benefits of integrated patient-specific information and fewer still have the benefit of specific drug formulary recommendations on the subject patient.

Drug formulary information is usually determinative of the cost-effectiveness of a prescription. Unwitting failure by a prescriber to follow formulary guidelines can impose unnecessary or unexpected cost burdens on the patient, or their benefits provider, and lead to poor patient compliance and aggravating and time-consuming disputes. The cost in dollars of non-compliance with drug formulary guidelines to benefit-providing corporations, insurers, health maintenance organizations and government providers, for example MEDICAID and MEDICARE, can be enormous. The cost of poor patient compliance may ultimately increase the total cost of care by generating a more serious, expensive adverse health outcome (emergency room visit, or hospital admission or death).

A difficulty in making integrated patient-specific information readily available to prescribing professionals is that the needed information components are not centralized but are widely distributed geographically and even when their geographic or electronic locations are known, are hard to access because of proprietary and liability and patient-confidentiality concerns and because of system, file or protocol incompatibilities.

Even in the computer-abundant United States, in the mid-90's, prescription writing is generally a manual process. After consulting with a patient to determine their problems and diagnosing, or attempting to diagnose their condition or disease, a physician selects a drug and a dosage and an amount to prescribe based upon their own personal knowledge and experience, if necessary using available reference materials which may or may not include promotional materials from drug manufacturers. A prescription is then written up under the physician's signature and bears a patient identification, a drug name, dosage amount and timing, refillability information and the physician's signature, the date, possibly an advisory regarding contraindications, and little other information. While a prescription may be typed, keyed or otherwise "generated" on a computer most prescriptions are still manually written.

Prescribing activity should be a good field for computerization, but one difficulty is the lack of apparent benefits to many physicians. Paper prescription pads are small and easily carried around by a physician. Manually writing a prescription will often be quicker and easier than using a computer, however good the system. The benefits of automated information systems often come not from greater data entry efficiency, but from the increased efficiency of the entire process, from the value of the transaction records generated and also from the control of the transaction entry process which may ensue. Physicians who are not computer-literate or who are even "computer-phobic" will require a most compelling reason to adopt a computerized prescription management system.

To be fully effective, a prescription management system must be readily usable by a wide range of physicians, preferably for all their prescribing activity must provide compelling value to patient care and increase overall treatment management efficiency. Providing an attractive computer-based system to physicians is fraught with unexpected difficulties.

Physicians and other health care professionals, especially those with prescribing authority, are representative of certain groups of professionals whose unique characteristics raise obstacles to the computerization of their day-to-day professional activities. Desirably, a computerized professional management system should be capable of flexible integration into their personalized and varied work flows.

Contrary to many perceptions and assumptions in conventional data-management systems intended for use by physicians, clinical physicians are not deskbound workers and do not usually have continuous access to a personal desktop computer during the course of their normal daily routine. To the contrary most physicians are ambulatory or even highly mobile, moving from room to room, from office to office, from hospital to hospital and to and from their car and home. While some physicians may spend the majority of their health care patient encounter activities at or near a desktop in their own office, such physicians are probably the exception. In clinics and hospitals physicians are often continually on the move between examination rooms, reception areas, administrative centers, hospital wards, specialist facilities such as radiology rooms and so on and so forth. In addition many physicians have more than one practice or more than one professional activity which takes them between an office or clinic and a hospital or other facility on a regular basis. Accordingly, it is a significant technical challenge to provide such mobile physicians with access to a computer-implemented management system that is readily available at the point of care.

Portable computers are a possible solution to the access problem now that powerful and compact notebook computers are widely available. Although currently available portable computers offer some advantages particularly to physicians moving between one work place and another, they also suffer certain drawbacks. One drawback is that external communication is difficult being commonly effected by moving diskettes, a valuable but limited method, or by modem connection to a telephone line which inconveniently requires plugging into a wall jack. Though possibly adequate for a physician having multiple offices, neither the communication means nor the portability of such systems is satisfactory for a ward physician moving from patient bed to patient bed. The weights and form factors of traditional portable computers are severe impediments to their assimilation into many clinical physicians' daily lives as dependable assistants to their professional work.

More recently, small handheld or palm computers known as personal digital assistants or personal information communicators have become available. An example is the Apple NEWTON (trademark). As of summer 1994, these are rather rudimentary devices as compared with desktop or full-powered portable systems, having modest permanent and RAM storage capacities and limited processing and communications abilities. Attractive to busy mobile professionals for their small size, such handheld computers can also embody highly desirable radio wave or infrared wireless communications abilities enabling them to exchange data with host systems without the cost or inconvenience of hard wiring.

Such portable hand held radio communicating computing devices are attractive for computerizing mobile professionals such as physicians, but their processing and storage limitations represent a real problem in providing a sophisticated, capable and attractive system for physicians.

A broad objective of this invention is to provide a prescription management system that can be used by physicians on such mobile computing devices.

Simply delivering a system on a convenient portable computer will not be enough to assure its regular use by a majority of physicians. Though highly educated and technically skilled, many physicians are not computer literate and are averse to confronting a computer screen. Some may even be intimidated by computers. Nor do their busy schedules permit time to learn complex or difficult systems. Even for an experienced user adoption of computer use into their daily routines requires time change and adaptation. With tremendous competition for their time, physicians will only be willing to take these steps if they are enticed by powerful system features that provides them with compelling value to patient care and overall practice management efficiency.

Nevertheless, the greatest of system features will be worthless if the system hinders the professional in executing routine functions. Even at sophisticated computer products companies with access to, and experience with, state-of-the-art systems, telephone sales staff often take down orders with pen and pad rather than using an on-line sales order systems.

An experienced professional practicing their specialty for example a pediatrician treating infants knows from experience exactly what to prescribe, in many instances. They will have neither the time nor the patience to work their way through conventional software selection and data entry procedures. Accordingly, a further object of this invention is to provide a prescription management system which personalizes itself to the prescribing patterns of experienced users.

SUMMARY OF THE INVENTION

This invention solves a problem. It solves the problem of providing a computerized, prescription management system that an average prescribing physician can use and will want to use and which makes possible significant improvements in the quality of prescriptions written. In preferred embodiments, the invention also solves the problem of significantly reducing prescription costs to patients and to their drugs benefit management company or government agency. The invention solves these problems for physicians by providing a prescription management system for electronic prescription creation by a prescriber at a point of patient care, said prescription being usable by a pharmacist to dispense drugs, said prescription management system comprising:

a) electronic posting means to select and capture in said prescription:
  i) a patient identifier;
  ii) a prescribed drug;
  iii) a dosage for said prescribed drug; and
b) a patient-condition treatment specification procedure;
whereby in creating said prescription said prescriber specifies a patient condition for treatment by said prescribed drug.

More generally, the invention provides a computer-based professional product specification system for use by other professionals, in addition to physicians, which can deliver substantial benefits to mobile-users who may be, computer-inexperienced.

By associating a patient condition or problem with each drug prescribed, a treatment objective is both expressed and recorded, . . . physician intent . . . and deliver for physicians the problem is solved by providing a user-friendly prescription management system, requiring minimal data entry enabling prescriptions to be created with an overall efficiency unobtainable by any known automated system and which can helpfully supplement the skills of the best of practitioners.

Pursuant to one preferred embodiment of the invention, the drugs in the drug list are classified according to a patient condition for which the drugs are effective and the onscreen drug selection procedure lists multiple drugs for treating each patient problem. In an alternative embodiment, the user makes a drug selection by generic or brand name or some other drug identifier, and the system supplies, suggests or requires, entry of an appropriate treatment condition so that the patient record is completed with the condition or conditions for which the selected drug is prescribed.

The invention also provides a user-adaptive prescription management system for electronic prescription creation by a prescriber at a point of patient care, said prescription being usable by a pharmacist to dispense drugs, said prescription management system comprising:

a) electronic posting means to select and capture in said prescription:
  i) a patient identifier;
  ii) a prescribed drug;
  iii) a dosage for said prescribed drug;
b) a patient-condition treatment specification procedure whereby in creating said prescription said prescriber specifies a patient condition for treatment by said prescribed drug;
c) an onscreen drug selection procedure having a patient condition list specifying multiple possible patient conditions, having a drug list specifying multiple possible prescribable drugs and having drug specification means to select and post a desired drug to said prescription; and
d) tracking means to track preferred data usage by a user and to adapt data displays to favor such preferred usage, whereby the system learns and adapts to a user's habits;
  wherein drugs in said drug list are classified according to a patient condition for which said drugs have efficacy and said onscreen drug selection procedure lists multiple drugs for treating each said patient problem.

Drug lists or individual drug selections or suggestions may be presented to prescriber-users in any of a variety of ways for example by frequency of prescription for a selected condition, based upon either the user's historical prescription activity or a wider base of historical prescribing activity, which could be nationally or regionally defined or derived from a drugs benefit house, health maintenance organization, hospital or other appropriate institution.

System suggestions for condition-related drug selection may be further refined into categories such as relative cost, generic or brand name and so on. Where many drugs are available for treating a patient's active condition, one particularly useful presentation is by multiple lines of therapeutic preference according to drug formulary guidelines. Thus, within the patient's particular formulary there may be suggested first, second and third lines of therapy. Different suggestions may be made for different patients according to the preferences of the patient's particular drugs benefit management company.

Preferably the system includes a comprehensive database of approved drugs classified by conditions for which they are known to have therapeutic effect and this database need not be maintained in the users station but should be accessible in real time to the user. Many valuable professional benefits are obtained by delivering a selective listing of drugs by condition to a physician. For example in treating a particular chronic condition such as gastro-intestinal disease, a physician may find that common medicaments such as antacids are ineffective, that a particular brand name drug such as TAGAMET (trademark) has, with prolonged use, undesired side effects so that the physician may at this point be interested in gaining information about alternative drugs with which they are less familiar. If the physician does not have the information at their finger tips, this could be a time consuming process in their office reviewing files and other archival information systems they have. Alternatively on-line electronic services may be used but this can also be a time consuming process. By offering a comprehensive selection of drugs known to be effective for a particular condition, this problem is easily solved for the physician. The preferred embodiments include back-up prescribing information on each drug, along with details of literature references supporting its manufacturer's therapeutic claims or with means enabling the physician promptly to obtain such references.

The invention is not limited to providing a prescription management system. It can provide, in the medical field alone, systems for clinical laboratory management, for medical record management for radiology management and the like. In addition the invention can provide novel professional data management systems that can create new products and yield comparable benefits in other professional spheres where professionals are responsible for specifying more or less complex technical products to solve client or customer problems.

In this wider aspect the invention provides a professional product specification system for electronically creating a technical specification usable by a professional to specify technical products said product specification system comprising:

a) electronic posting means to select and capture in said technical specification:
  i) a customer identifier;
  ii) a specified product; and
b) an onscreen product selection procedure having a product benefit list specifying multiple possible customer benefits having a product list specifying multiple possible specifiable products and having product specification means to select and post a desired product to said specification;
  wherein products in said product list are classified according to a customer benefit which said products can provide and said onscreen product selection procedure lists multiple products for providing each said customer benefit.

BRIEF DESCRIPTION OF THE DRAWINGS

By way of example, some preferred embodiments of the invention are described in detail below with reference to the accompanying drawings in which:

FIG. 7 is a nonformulary drug selection screen;

FIG. 8 is an alternative condition-specification and drug selection screen;

FIG. 9 is an alternative direct drug specification screen;

FIG. 10 is a condition selection screen, drug specified;

FIG. 12 is a single prescription history screen.

DETAILED DESCRIPTION OF THE PREFERRED EMBODIMENTS

Overview

Figure 1:
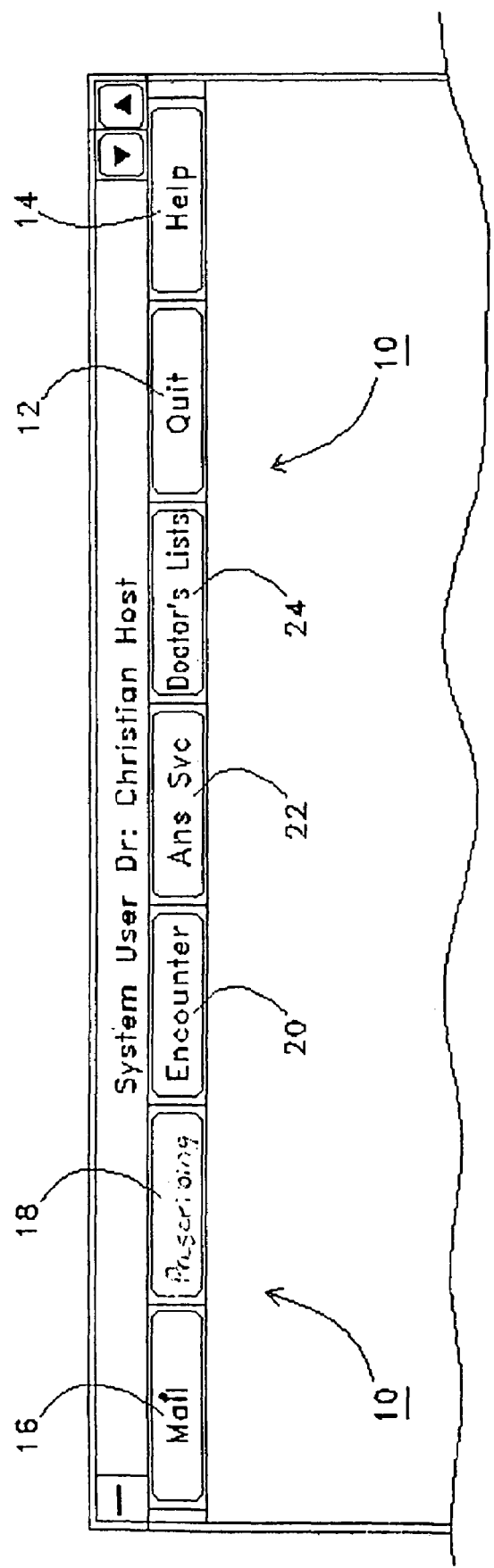
FIG. 1 shows a system entry screen of a prescription management system embodiment of the invention which system incorporates the screens of FIGS. 2-11.

The prescription management system illustrated in FIGS. 1-14 can be provided in software for single-user operation on a stand-alone personal computer for use, for example, by a sole practitioner or for multi-user operation on a local area network for use, for example, by physicians and other prescribers within a single facility, hospital, group practice, or the like prescribing organization, and the invention can bring substantial benefits to such users and their patients.

However, more significant benefits can accrue to patients, physicians, drug benefit providers and the public at large by implementation of the described prescription management system on a regional or nation-wide basis. To this end, a preferred embodiment of prescription management system comprises a host computer facility supporting wired or wireless network delivery of user-relevant components of said prescription management system to multiple remote user interface devices.

The host computer facility provides data, or access to data, data processing and communications resources for users to draw upon via the user interface devices. The host computer facility can be a server or cluster of servers with associated data storage volumes, and at least one intelligent client providing access to the server or servers. As will be explained in more detail hereinafter, especially with reference to FIG. 16, the host computer facility can call upon a variety of external resources and functions as a marshalling and processing center for organizing resources into useful and manageable pieces for utilization by limited capacity user-interface devices. In a preferred embodiment it is a co-ordination point on a network for a number of user-device clients. Preferably the network accesses or includes a number of remote database sources providing useful information elements to the system.

Referring to FIGS. 1 to 14 of the drawings, the screens shown employ user-friendly data selection and data entry devices such as are familiar to many computer users in Apple Corporation's Macintosh® (trademark) and Microsoft Corporation's Windows operating systems, for example activatable buttons, pointers, scroll bars, icons, arrow key, drop-down menus, windows and other screen symbols designed for actuation by a pointing device, for example, a mouse or trackball. More preferably, for compact "pocket-book" computer applications, the pointing device is a pen or stylus.

The prescription management system shown in this embodiment of the invention has been designed for implementation on physically compact, portable, user-interface devices such as small portable personal computers, especially hand held devices known as personal digital assistants. Those skilled in the art will understand that the system can readily be used on or adapted to other hardware platforms, for example, a physician's desktop computer and can be expressed in different software interfaces from that shown, especially ones that use different input devices such as keyboards, touch pads or touch screens and the like.

Pursuant to certain user-adaptive aspects of this invention, the screens automatically personalize themselves, with use, to adopt the patterns and habits of a regular user of a particular device platform for the system, offering the user their most frequently used information, drugs, conditions, patients or patient groups, and so on as first line choices. This adaptive characteristic is a valuable benefit endearing the system to experienced users who may become impatient with hierarchically accessed data.

Ease of use and suitability of the system to keyless or minimally keyed platforms, especially PDA's is promoted by minimizing the need for actual text or data entry by the user and by emphasizing instead data selection from extensive, preferably comprehensive, data lists. Preferred embodiments of the invention allow quick pen selection of data items through columnar pick lists.

The data lists, categories, groups, addresses or routes, can be organized in multiple hierarchies for rapid and flexible access to multiple large, remote databases, via multiple access routes to retrieve multiple related data elements and assemble them into a single data file, for example, a patient history file compiled from the data resources of a patient's historical health providers.

A desirable goal is to provide the physician-user with intelligent data lists that are, where possible, exhaustive and list, for example, all prescribable drugs, all conditions, all formularies or all patients and present the physician with helpful first-line choices or defaults selected intelligently on the basis of historical data known to the system. Preferably, the selection means is fully system embodied, or automatic, operating transparently to the user and requiring a minimum of configurational or setup operations by the user.

Virtual Patient Record

An ability to compile what may be termed a "virtual" patient record from multiple remote databases of primary source information is a valuable novel feature of preferred aspects of this invention. Such a virtual patient record can be created in a chronologically current version by online interrogation of all possible primary sources of electronically recorded patient history elements, by retrieving those elements and assembling them into a complete record. Yet the record need neither be drawn from, nor committed to, permanent storage, obviating storage requirements for accumulations of patient records.

The record can be assembled dynamically, on an as-needed basis, consulted by an authorized system user, and then dissolved, without ever having been saved, giving the record a virtual character.

Record element retrieval and record assembly are conducted under the auspices of the host computer facility employing a novel patient data directory service providing routing information to each patient's record elements. For each patient, the patient data directory service lists all institutions, including independent physicians, hospitals, HMO's, insurance companies, and so on, known to have source historical records on that patient, against a unique patient identifier, such as described hereinbelow. Also listed are routing or address data enabling the host facility to access institutional databases to retrieve record elements. Access protocols detailing, for example, what data can be accessed, when it may be accessed, by whom or by what organization or department it may be accessed, can be kept in a patient-specified directory, or elsewhere.

Patients not listed in the directory service can be searched at the remote source databases and, optionally, at other, host computer facilities supporting the inventive system for other groups of users.

The complete, assembled patient history, or record, need never be stored, unless the patient requests or consents to such storage, and it serves some useful administrative or care-related function. Storage or archiving of a record that is potentially updatable from multiple uncoordinated locations has the drawback of dating it. To become current, the record must be refreshed from any database containing a new data element for that patient.

By using a dynamically assembled virtual record, and never storing it, potential problems of maintaining patient confidentiality and preventing unauthorized access to highly sensitive personal information can be mitigated or avoided. This aspect of the invention avoids proliferation of a patient's confidential history and permits primary source data proprietors to act as exclusive wardens of their individual confidential data elements.

Bio-Pattern Recognition

Bio-pattern recognition of personal user characteristics including, for example, handwriting, signatures, voice patterns and fingerprints is an attractive medium for accepting user inputs, but in the present state of development of the technology, suffers drawbacks which disfavor use of bio-pattern recognition in preferred embodiments of the invention. Future developments such as greater processing capabilities in small user-interface devices, and more accurate and efficient bio-pattern recognition techniques may change this picture and favor adoption of one or more forms of bio-pattern recognition.

Thus, handwriting recognition, is eschewed in preferred embodiments of the invention, at the present time, because writing is more tiresome to the user than pointing, pressing or clicking and adds complexity and processing overhead to the system. Additionally, handwriting recognition, although presently available in pioneer systems, adds uncertainties, may require significant user effort or adaptation and may threaten data accuracy or promote user error.

Signature recognition may be desirable, if permitted by regulatory agencies, for remote electronic authorization of fulfillment at the pharmacy especially for mail order prescription fulfillment and the pharmacy-prescriber link can, if desired, add additional levels of security by transmitting or exchanging supplemental electronic identifiers.

However, better security, in terms of ensuring that the filled prescription is released to the intended patient, or their agent, may by provided, by treating an electronic prescription transmission to a pharmacy as an advisory against which fulfillment may be initiated, while the prescription is released only in exchange for a manually signed hard (paper) copy. Signature recognition or transmission as an individual graphic element, insofar as it may be useful or required in the prescribing process, can accordingly be incorporated in systems according to the intention. Processing demands on the user's device can be minimized by confining the device's capabilities to recognition of the signatures of only those users authorized to use that particular device.

Adding higher performance hardware to support the processing needs of handwriting recognition may be impossible with available technology if a preferred lightweight, compact form factor is to be retained for the user's device. An aim of the invention is to provide a qualified prescribing professional with a valuable tool that imposes no significant burdens of weight or volume on the user, that demands little of their time and yet can respond rapidly, delivering valuable drug and patient information to the user from remotely located, disparate sources. In other words, an aim of the invention is to provide an intelligent, knowledgeable computerized prescription pad.

This aim could be compromised by adoption of handwriting recognition technology at the date of this application. Similar problems apply to voice recognition as a significant data input medium. Either or both handwriting and voice recognition may be valuable enhancements of future embodiments of the inventive systems especially if future technology makes these capabilities available on smaller user devices. In particular, limited voice recognition may be valuable as a user identifier for password access or as an authorizing signature.

Security

Security may be provided by password protection operating hierarchically on one or more levels, to provide varying degrees of access according to the user's level of authorization, as desired. Additional password or numeric code control may protect sensitive system-accessed information, for example, patient records, or parts thereof, or physician-user data, including personal lists and prescribing profiles.

Patient record access codes can, in selected instances, be patient provided, or granted by intelligent security control cards, having been furnished to the patient by a system administrator, or agent, prior to the physician encounter. Physician or other user access to a patient's record, or to sensitive details thereof, can thereby be restricted to a need-to-know basis. Access by third parties to physician-related data can be similarly protected.

Provision for override of such security features should be available, for example for an emergency room doctor, and is allowed on a special case exception basis, is auditable, and traceable to the overriding user.

Password-controlled access to many computer networks is often workstation dependent with each workstation using a unique password to access the network. Although user passwords may also be employed, these are often workstation-dependent, for example, being incorporated in the workstation's login scripts. In contrast thereto the present invention prefers that user access to the host computer facility be device-independent so that a given user can access the system via any of numerous devices, provided they have the right password or passwords. By this means, users are not dependent upon a single device that may be lost or misplaced.

A still more preferred feature is to have user passwords which link each user with an individual profile or style sheet on the host computer facility representing the user's patterns of preferences so that the user-customization features of the system, which will be described more fully hereinafter, are readily available to the user independently of the particular interface device that happens to be employed for accessing the system.

These and other device-independent features can permit the prescription management system to be fully operative without committing useful data to storage on the user device. This is a valuable security feature. In the event of theft or attempts at unauthorized use, even by skilled third parties, a user device will be worthless as a means to access sensitive data on the system or to use the system illegally.

Optionally, lost or stolen devices can be deactivated by the application or by system software, after user notification, by erasing or otherwise rendering device-resident application procedures inoperable, without loss of device-resident data. Use of a virtual patient record, as described herein, which need not be stored locally, is a valuable safeguard against unauthorized access of confidential data on lost, stolen or "borrowed" user devices.

Host Computer Facility

Currently contemplated preferred embodiments further control the processing and storage demands placed on the user's device by intelligently delegating data-processing and storage activities to a linked remote, host computer facility, as referenced above, to the extent warranted by the capabilities of the user device. Thus, for example, a comprehensive drug database may be stored and maintained on such a host computer facility with selected data, for a particular drug list or an individual drug's formulation characteristics, being forwarded to the user's device on an as-needed basis, then being eliminated from the user device when no longer required. Other activities may advantageously be performed locally on the device, such as dynamic assembly of records from elements retrieved across the network from remote storage, and storage of the user's personal or most frequently referenced data and data lists, where the device's capabilities permit.

Where the user device is more powerful than present-day PDA's, for example a present-day desktop computer or perhaps the PDA's of the future, more processing and data storage functions can be retained at the user device rather than delegated to the network. Although permanent (disk, diskette or flash memory) storage may have uses, security concerns can be better managed on the network than on the user device, so that it is preferred that minimal data be permanently stored on the user device. Accordingly physical storage resources of limited user devices are preferably allocated to RAM rather than permanent storage.

Advantageously, a user profile can also be stored on the host computer facility so that if the user device is lost, broken or stolen, a new device can be automatically reconfigured across the network linking the user to the host facility, so that the application behaves the same.

Preferably such a host computer facility also provides customized services to each user device, performing "user-adaptive" functions for that device, as described herein, to adapt it to its authorized user or user's prescribing behavior and improve the level of assistance provided to the user. Employing such off-loading techniques, permanent storage capabilities of the device can be minimized in favor of faster RAM storage capabilities.

The screens are designed to be non-intimidating to computer-inexperienced professionals and to present familiar information and terminology to them while avoiding specialist computer jargon. Individually, they are easy-to-use for novices yet rapid enough for experienced users. Collectively, they provide an appealing system interface which can flexibly integrate into a physician's personal work flow.

In addition, the screens are laid out in the manner of appealing logical forms that echo familiar data formats encountered by a physician in their day-to-day work. An important objective is to make the screens self explanatory within the professional's normal terms of reference so as to avoid any need for access to help, although of course, HELP buttons can be provided if desired and extensive help documentation can also be provided. System utilities such as indexing, setup and purging are either concealed from the user or removed for execution on a remote host computer facility. Data integrity and availability responsibilities are also delegated to the host computer facility, or its remote data suppliers. Thus data saving, archival, backup and data-replication functions are host facility responsibilities, not concerns of the user.

The system is designed to require a minimum of actual text or data entry. So far as possible, item entry is effected by selection from lists of items, for example by highlighting an item, then clicking a mouse, or more preferably penning, to activate an item.

The prescription management system is made as user-friendly to physicians as possible, for example, by using familiar professional terminology and abbreviations. Thus terms such as "Patient" or "Pt", "Drug" or "Rx", "Condition" or "Dx" and "Treatment" or "Tx" are used rather than confusing generalities such as "subject" and "item" that often appear in generic software. The Prescription Management System shown in this embodiment of the invention has been designed for use with small portable personal computers, especially hand held devices known as personal digital assistants. Those skilled in the art will understand that the system can readily be used on or adapted to other hardware platforms, for example, a physician's desk top computer and can be expressed in different software interfaces from that shown.

Referring now to FIG. 1 the system entry screen illustrated has a user-customizable button bar 10 which has been set with a conventional Quit button 12 and a Help button 14, along with a Mail button 16 for accessing an electronic mail ("E-Mail") system, a Prescribing button 18 for accessing the prescription management system embodiment of the invention, an Encounter button 20 for accessing a patient encounter management system (not further described herein). Ans Svc button 22 accesses an answering service screen (not shown), which as a convenience function can be dynamically linked via the host computer facility to log incoming calls for the user. The answering service is preferably intelligent and prioritizes, by flagging or displaying, patient- or treatment-related calls, for example those from a pharmacy, while screening out or de-prioritizes less relevant calls.

History-Cognitive Drug and Condition Listing

A Doctor's Lists button 24 accesses a more or less complex display of patient condition and therapeutic drug lists. Preferably, the drug and condition lists are linked together to associate a drug with one or more conditions for which it might be prescribed and, in most cases to provide the physician user with a conveniently displayed, concise selection of drugs for treating any particular condition. In a preferred feature of this invention, the system has a user-adaptive character and adapts itself to the user's habits and prescribing patterns so as to service the user more efficiently. To this end, the drug lists or the condition lists, or both are system-modified with use to reflect the prescribing frequency of particular drugs or the frequency of occurrence of particular conditions. Thus, more frequently prescribed drugs or more frequently encountered conditions can be presented to the user physician in a more prominent manner or more immediate manner than ones found by the system to be historically less common in the particular user prescribing environment. In this way the system becomes more valuable with use as the drug and condition lists develop into personalized lists featuring the user's preferences.

With such cognitive features the inventive system is effectively cognizant of ongoing prescribing activity. It comes to know its user's environment and preferences, can adapt itself to any number of specialist situations, and can, if suitably equipped, subtly prompt the user, online with original, relevant but elusive information derived from the user's computer-memorialized practice experience. For example the system may prompt the user that the last time Drug X was prescribed for Condition Y, Patient Q reported adverse reaction Z. Where the host computer facility documents a catalog of known adverse reactions to system-listed drugs, a system enhancement can report new adverse reactions to the user or centrally, to the host computer facility, by tracking logged patient conditions and relating them, where appropriate, to a previous prescription. In similar manner the system may log drug-drug interactions, which interactions can also be associated with a target condition or conditions. Many other valuable retrospective statistical studies and analyses are made possible by deployment of the invention, as will be apparent to those skilled in the art. While such studies are potentially of immense public value if widely implemented, careful controls will be required to avoid reporting unrelated conditions as adverse drug reactions.

With time, as it adopts appropriate specialist prescribing patterns, the user-adaptive prescription management system of the invention can be just as relevant and useful to, for example, a specialist in tropical medicine as it is to a pediatrician. This desirable result can be achieved without encumbering either specialist with the needs of the other.

Those skilled in the art will appreciate that the invention's cognitive, user-adaptive features employ significant programming routines and procedures and are quite different from common, user-responsive software defaults which merely offer defaults pre-set by the user or simply show the last used item, file or the like as a default.

If desired, the user's prescription management system can have built-in, online, statistical reporting functions enabling a physician user to review their, or others, historical experience with a particular drug or condition and providing online historical review of any other activities or data entrusted to the system.

Of scientific note is that the system is privy to and operates at the confluence of three powerful emergent data streams: encyclopedic data on therapeutic agents intended to moderate particular conditions or patient problems; data on individual prescriber activity using skill and judgment to diagnose conditions or problems and make prescribing decisions selecting and applying therapeutic agents to diminish diagnosed conditions; and patient history data recording not only prescribing decisions but also the results of those decisions (see the description of FIG. 12, below). Thus, the system captures not only prescribing activity but also the prescriber's intent, the problem or condition targeted by the prescriber in specifying a particular drug, and can track the success of that intent. The linkage of treatment with condition treated captures the reason why the doctor took the prescribing action that was taken. This intent may, and can legally, be different from approved FDA therapeutic indications for a drug.

Of commercial note is that the foregoing data may be aggregated for multiple users, for example by the host computing facility, for market research purposes. Also, an individual user's prescribing patterns may be reviewed by the user or by others. For example, drug benefits companies, can review the user's prescribing patterns for formulary compliance and respond by encouraging better compliance, where appropriate. Release of such data to third parties can be controlled to safeguard the privacy of the prescriber, or other health care provider, by prescriber-determined data access protocols specifying who, or what organization, department or group, may access what data, when they may access it and what they can do with it. For example, one physician may permit academic use for research studies and prohibit commercial use while another may permit either.

As will be described in more detail subsequently, a range of optional features, for example the answering service and e-mail features mentioned above, or other communications features, can be made available from button bar 10 providing the user with user-configurable means to customize the system to their personal needs and tastes.

Intelligent Drug-Selection Procedure

Skeptical prescribers are encouraged to adopt the prescription management system of the invention, by its ability to bring to the point-of-care, in readily utilizable form, a battery of relevant drug-specification information and important patient-related information, much of which is not readily accessible at the point-of-care by conventional means.

Preferred embodiments of the invention achieve this desirable result by providing an intelligent drug-selection procedure which is supported by transparent connectivity to multiple remote proprietary information systems at the point of care, enabling a physician to draw upon the following categories of data:

i) physician-user prescribing-frequency data;

ii) patient drug formulary information as to a drug's status with a patient's drug benefits provider;

iii) drug dosage characteristics, for example, form, size, route of administration, amount, frequency and the like;

iv) drug-specific treatment information as to condition-related efficacy, and preferably as to contraindications and adverse reactions;

v) relevant patient history information as to current and previous prescriptions, and preferably also, pursuant to the teaching of the present invention, problem-history information; and vi) laboratory and other diagnostic test information related to the patient's indications, to dosing, to therapeutic choices or to specific drug selections.

Preferably, this data is brought to the point-of-care by relying upon retrieval from remote source databases at remote facilities responsible for capturing original update data, and not by relying upon redundant non-source data requiring constant synchronization with source data to remain current.

Diagnostic Tests

Items i)-v) above, will be described in considerable detail hereinafter. With regard to diagnostic tests and procedures, for example radiology, the invention contemplates electronically bringing relevant information to the point of care to assist health care providers make informed decisions. Such diagnostic information may comprise recommendations for clarifying a tentative diagnosis, or choice of diagnoses, or may comprise diagnostic results that can be used to make more informed therapy decisions and, in particular, to make better therapeutic drug selections. Body system function tests, for example renal or liver function tests are clearly valuable to a drug selection process, since renal and liver condition are important in determining dosages of some medications. Other therapy-relevant diagnostic determinations can usefully be presented at the point of care, by means of the present invention, for example, drug-level determinations can enhance dosing decisions.

Patient Encounter Program

Figure 2:
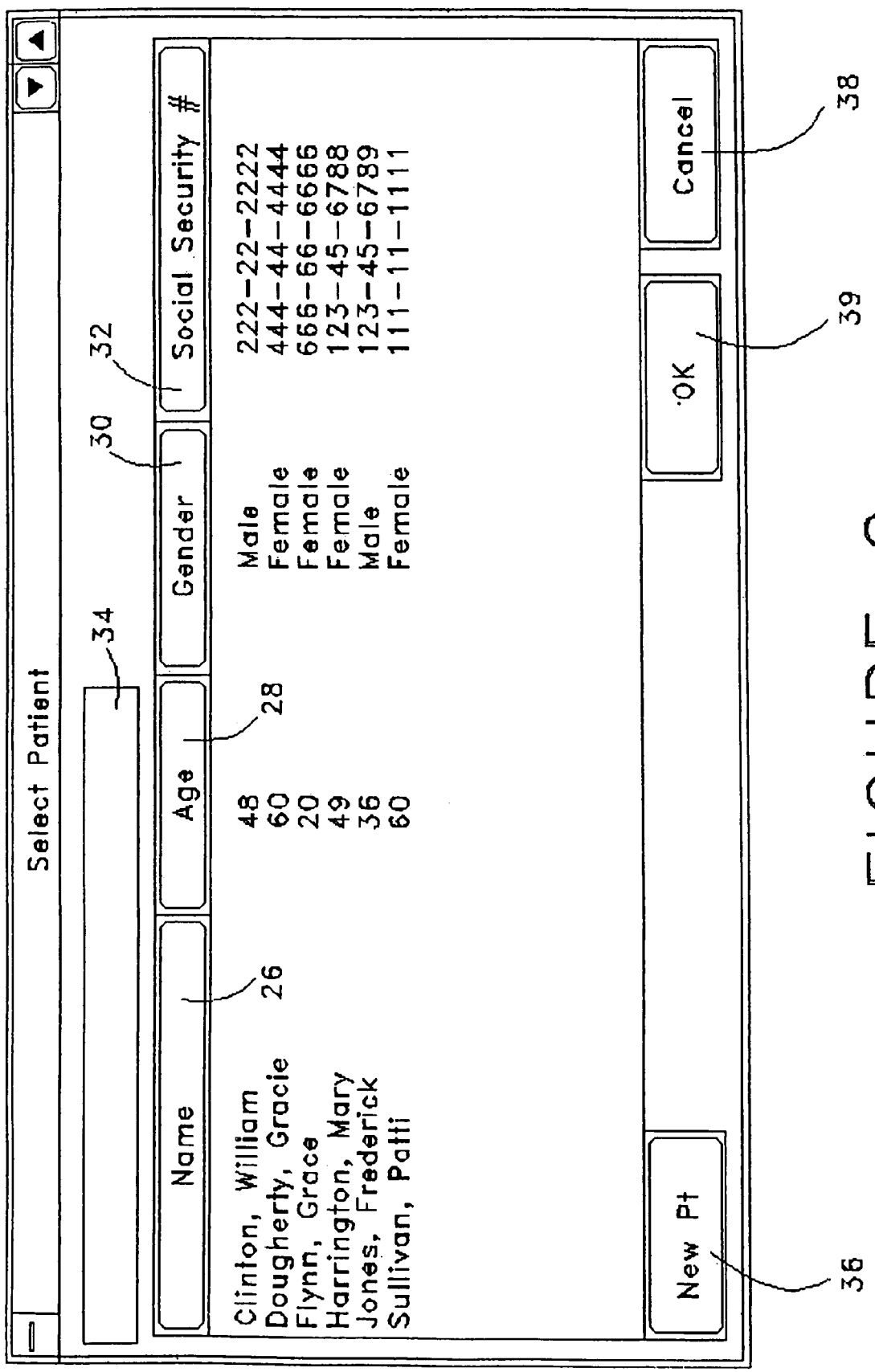
FIG. 2 is a patient selection screen.

A useful, prescription management system-compatible patient encounter program can begin with a patient selection screen such as that of FIG. 2. The patient selection screen of FIG. 2 can be activated by any one of multiple programs which may, for example, be initiated via the system entry screen of FIG. 1, but could be independent, free-standing programs or any other program for which the ability to create, update and modify a patient-specific record or a patient history is valuable.

Preferred embodiments of software procedures (or programs) associated with the novel patient record selection procedure illustrated in FIG. 2 can access multiple remote databases to retrieve patient records, for example, by using the host computer facility, and can also post new patient records, and updates, created locally by the physician-user, to the multiple remote databases in real time, or in batch mode.

Patient Record Source Data

Source data for a typical patient record may be distributed across multiple, geographically dispersed, electronically incompatible, remote databases maintained for example by drug benefit companies, insurers, laboratories, medical facilities, diagnostic testing facilities and health maintenance organizations, including government agencies (MEDICAID, MEDICARE, etc.) and health care providers themselves, that have serviced the patient in the past. Known automated patient record systems either ignore such remote data and work only with data created at the maintaining facility or vertically integrated health care organization, or create and maintain duplicates of the remote data.

Still more preferred embodiments of the invention provide substantial savings of resources, time and effort by using only source data for patient records, minimizing creation of multiple redundant local databases that require constant synchronization with remote sources if they are to remain accurate and up to date.

The invention also provides novel data-retrieval network systems to retrieve relevant patient data elements from multiple remote heterogenous primary source databases. Preferably, every time a host computer facility receives a call from a user device for a patient history or patient record, relevant data elements, for that record, or a record component (e.g. the most recent six-month or twelve-month portion), are retrieved from remote source databases, dynamically assembled, or integrated, into a virtual patient record, as described above, and delivered to the user device as an integral system data set. Alternatively, record assembly, which does not require undue hardware resources, can be performed on board the user device.

The record is viewed and may be printed out by the user, with patient authorization, but does not need to be permanently stored.

The host computer facility responsible for dynamic assembly of the virtual record logs the time, date and calling user to provide an audit trail of access to the patient's record, but does not commit the record to permanent storage. After use, the virtual patient record disappears, although it can be reconstructed archivally.

If the record is required again, it is assembled anew, thereby incorporating any updates that may have occurred in the interim, for example changes in drug benefit status, insurance coverage or the like, newly generated laboratory, radiology or other diagnostic results, or other, e.g. emergency, prescriptions dispensed. The act of assembling a record externally of its sources immediately dates the record: it is cut off from any updates, and therefore liable to become incomplete, obsolete or dated. Virtual patient record assembly, as described herein, avoids this problem making local storage of patient records unnecessary.

Transactions are archived by the host system to provide a complete transaction history, so that past activity can be reconstructed. Such a data-reconstruction capability to provide clear hind vision of the patient's record at any given time is an important medicolegal capability. That historical version is preferably reconstructed from a transaction log and assembly of timed and dated record elements, or segments, in a manner not unlike that used by version control software.

Creating a virtual patient record permits optimal data currency and accuracy and, by avoiding unnecessary redundant copies of patient data minimizes liability for misuse or unauthorized access. Patient confidentiality can be maximized and is verifiable by the system-generated audit trail.

Preferably for individual record elements to be admitted to the system, they are required to be at least dated and preferably also to be timed at source, such timing and dating relating to whatever event created the record. In addition to its value as an integral record characteristic, chronological data is useful for retrospective archival reconstruction of a record as it existed (in its elements) at any given point in time. This can be achieved by retrieving record elements, as described above, using a suitable date filter and if appropriate, a time filter, to include only those (or selected ones of those) record elements that existed at the desired given point in time.

Such an archival retrospective record reconstruction capability is a highly desirable adjunct to the virtual patient record described herein permitting full creation and examination of any desired historical records, such as may be required for review or legal purposes.

Using the above-described method of dynamic retrieval from remote databases across a data-retrieval, record-integrating network, source database proprietors can remain wardens of the only copy of that data and obtain patient authorization to be the sole repository of that data. Laboratories can keep laboratory records; insurance companies can keep insurance records; hospitals can keep hospital records; and health maintenance organizations can keep their own records; without ever having to release copies of these records into external electronic storage by third parties, with the security hazards attendant upon such releases. Any electronic release made externally using the data access control features described herein can be assured of always being authorized by whatever entity, be they patient, physician or organization, that has proprietary rights in the data.

FIG. 2: Patient Selection Screen

Upon selecting Prescribing button 18 by clicking or pen contact, a patient selection screen, for example as shown in FIG. 2, is displayed as a preliminary to prescription management functions. Referring to the patient selection screen of FIG. 2, the name, age, gender, and social security numbers of patients who have authorized the user physician to treat them, or to access the system on their behalf, are listed under respective column header buttons, namely, Name button 26, Age button 28, Gender button 30 and Social Security # button 32.

Lists can be scanned, or text entries made in a blank search box 34 at the top of the screen, using string or full name searches to locate the desired patient or to review the patient list. Column headers 26-32 can be clicked or touched to sort the patient list on any of those fields and activate search box 34. Search box 34 is linked to the sort fields so that, for example, if the listing is sorted by social security number then alphabetical entry attempts are rejected from search box 34 and numeric entries are used as social security number locators. The characters can be keyed or system provided from pop-up screens, or voice or handwriting recognition may be employed.

Figure 3:
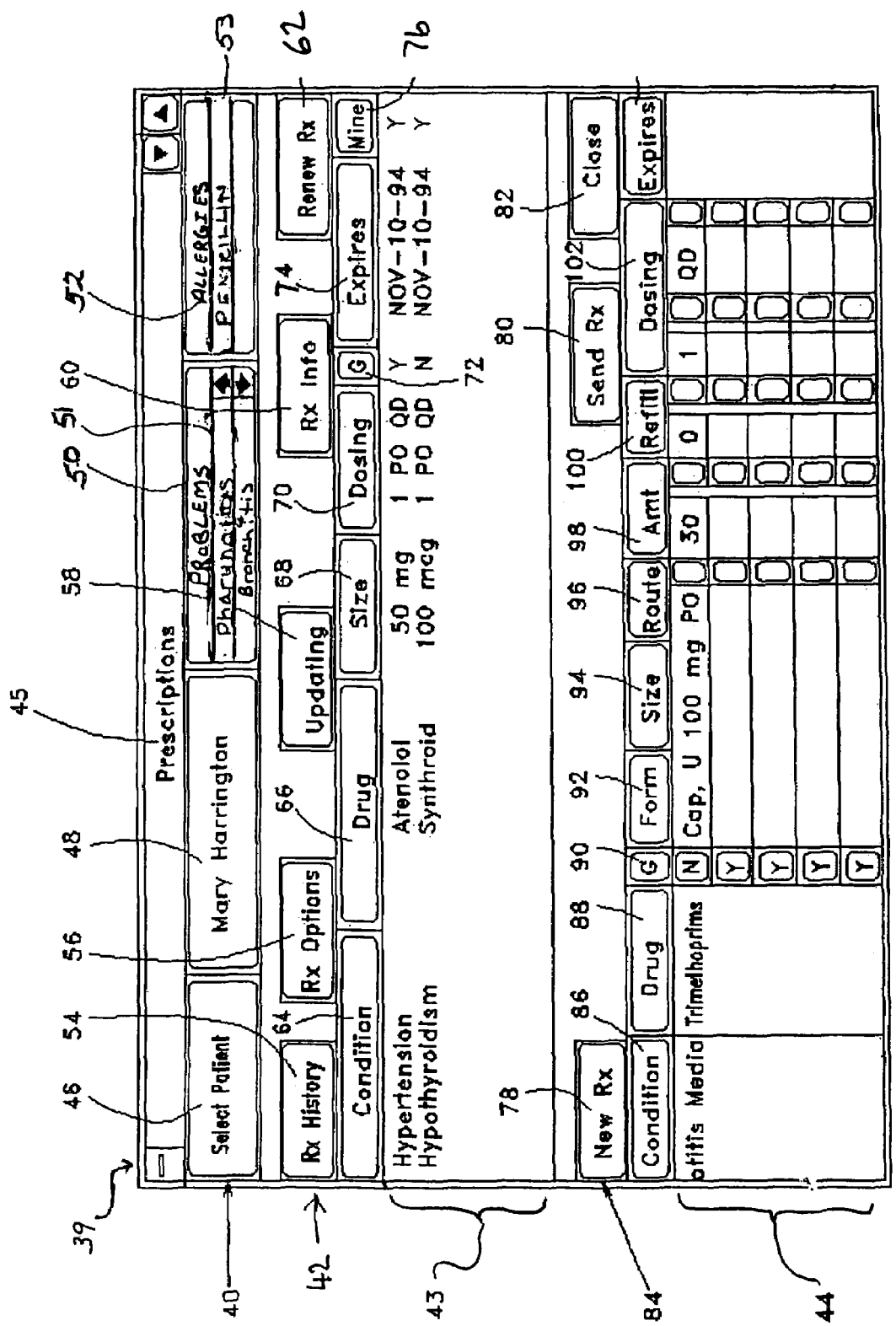
FIG. 3 shows a prescription creation screen.

New Pt button 36 activates a new patient entry bar, while the Ok button 39 accepts a highlighted patient selection and advances to the prescription management screen of FIG. 3. Cancel button 38 returns to the system entry screen of FIG. 1.

If desired, preliminary selection of groups of patients can be made by providing various patient lists, for example "Today's Patients", "In-Patients", "Out-Patients", "Private Patients" and the like. Such patient lists are preferably system-maintained, on an ongoing basis, using the latest data available to the system and preferably enable the user to select a convenient group of patients that has a high probability of including the next patient or patients to be encountered, thereby speeding access and retrieval of a desired patient record. Where the user typically encounters patients in groups, for example one group in an out-patient clinic and another group in an in-patient clinic, such grouping of patient records into lists also facilitates organization by a host computer facility of display data into small batches that can more rapidly be communicated via limited capacity copper wires and modems and are of a size that can conveniently be held in RAM on a small, portable user device.

Patient Data Security

Critical to public confidence in the prescription management system of the invention are issues of security, since the system requires access to personal records. Many people will fear unauthorized access to or use of their personal information. Preferably, the invention provides careful controls to alleviate such fears and to prevent unauthorized access to a patient's data or to their physician's prescribing profiles.

Preferably also, the system, or an associated support network, provides data access controls such that the only accesses that can occur are those that have been authorized or preauthorized, at a point of care or elsewhere, in accordance with security profiles on the network established on behalf of data-proprietor entities such as patients, physicians or organizations. It is further preferred that the entity's security profile, or filter, details what data can be accessed, when it may be accessed, where it may be accessed and by whom it may be accessed.

Various suitable data access control measures will be known to those skilled in the art and considerable security can be obtained by using more or less complex identifiers for patients or for physician-users of the system or for both.

Patient records should use a standard identifier to be clearly and distinctly identified with a confidence level appropriate to the expected patient population in the lifetime of the system so that the records of patients with similar or identical names are not confused. If desired, a coded alphanumeric patient identifier (not shown) may be used. Alternatively, or in addition, other unique patient identifiers such as social security numbers may be used alone or as secondary references in conjunction with patient names and the like.

More relevant to security is proper identification of a user to whom patient data is released or from whom new data is received by the host computer facility. While numeric or alphanumeric user identification codes provide some level of security, higher levels are provided by using graphic, photographic or fingerprint recognition to identify a system user.

More preferred embodiments of the invention can ensure a still higher level of confidentiality by automatically maintaining a complete audit trail of access to patient data. Preferably the audit trail details, for every access, who or what organization accessed the record, what part of the record was accessed, when it was accessed (both date and time) and what was the purpose of viewing the record. Thus, associated with every patient record is a timed and dated log of every physician user, organization or health care professional accessing that record. If desired, the log can be reported, or made available to a patient, on request, for example through online access (with careful security controls), via print or fax, and so on.

Patient-directed control of the flow of their own data, a novel concept in medical or health care information systems, can be achieved by centrally inputting at the or a host computer facility patient-generated record-access specifications to determine which users, or user organizations or departments (for example clinics), can access what data during what period and what uses can be made of the data. Clearly, such specifications must not deleteriously restrict physicians in the execution of their professional missions. Such record-access specifications or profiles could be maintained at a remote database rather than the host computer facility. Thus, access to their records is controlled by patients and individuals and organizations can be given patient-defined, selective access or access based on a need to know, or a patient may block access to all data flow, if they wish. In emergencies, physicians may be able to override a patient security block, but such events are recorded so that any abuse can be monitored and action can be taken to discourage abusers.

MD-Related Data Security

Many similar data security considerations apply to prescriber-related data. Used comprehensively, as it is intended to be, the system is privy to full particulars of a physician user's professional prescribing behavior, day in, day out, potentially throughout their career. System resources may be used to compile any desired historical record of a user's prescribing activities. Patient-confidentiality aspects of this data have been addressed above and can be satisfactorily managed by controlling access to patient-related data in accordance with a patient's previously, or currently expressed wishes, as described herein. In addressing physician-oriented prescribing issues, the historical record may be rendered patient-anonymous by stripping the data of recognizable patient identifiers, or aggregating the data. The resultant historical prescribing data can communicate significant information about the prescriber, is personal and proprietary to the prescriber.

Pursuant to this invention, the prescriber's rights in their historical prescribing data are protectable in a manner similar to the protection affordable to patients, by providing prescriber-determined access control specifications detailing permissible levels of third-party access to prescriber data. Such prescriber data access control specifications can be stored in individual files on the network and can comprise as to who or what organization, or type of organization may access what data, for what purpose and for what period of time such access right may be effective. Clearly, multiple levels of access control may be described to any desired degree of complexity. User preferences may include user authorization for data access by various third parties for example health maintenance organizations (HMO's), hospitals, government agencies, managed care organizations and so on.

A particular group to whom a prescriber may wish to yield access rights comprises collective bargaining associations, for example independent practitioner associations, preferred provider organizations and physician hospital organizations. Preferably, all accesses to a prescriber's data are system stamped with a date, time and accessor ID, to create an audit trail of such accesses, similar to the audit trail left by accesses to patient data.

System-determined access control can be invoked, whenever a prescriber data access request is received, by referencing the prescriber's access control file and permitting or denying access in accordance with the file's specifications.

Prescription Creation Screen 39

Referring to FIG. 3, prescription creation screen 39 has a full array of user-activatable buttons enabling a physician to draw on powerful resources within the prescription management system and supporting it in the host computer facility and associated data-retrieval network, as will shortly be described. Near the top of screen 39 is a patient features bar 40 below which a prescription features bar 42 coordinates all features necessary to review current therapy and order changes in treatment, or order new treatment, for the selected patient. A prescription history zone 43 extends across the middle of the screen, the lower screen portion contains a prescribing zone 44, and a screen title 45 appears at the top of the screen.

Patient features bar 40 comprises a Select Patient button 46, a selected patient indicator 48, in this case Mary Harrington, a patient Problems button 50 and a patient Allergies button 52. Beneath Problems button 50 are displayed Mary Harrington's currently active problems 51 or conditions, shown here as pharyngitis and bronchitis. Beneath Allergies button 52 are displayed Mary Harrington's known allergies. Pressing or otherwise activating Problems button 50 or Allergies button 52 opens a window or screen listing problems or allergies from which a physician, or other professional user, can select new problems or allergies to add to Mary Harrington's record, or delete ones that are no longer active.

Optionally, system-provided problem or allergy libraries may be organized into multiple lists with button 50 or 52, respectively, opening a list selection box as a preliminary to displaying a selected problem or allergy list.

Problems or conditions 51 and allergies 53 are here displayed as a helpful notation for the prescriber and do not become prescription elements as a result of being selected for display in this part of the screen. However, selections made here are functional in that selected problems 51 (conditions) will become defaults or preferred choices in a subsequent condition specification procedure and the system will review any drugs prescribed for relevance to allergies 53.

Prescription features bar 42 comprises an Rx History button 54, an Rx Options button 56, an Updating indicator 58, an Rx Info button 60 and a Renew Rx button 62.

Prescription history zone 43 displays those historical prescription details that may be relevant to a current prescription and has a Condition field 64, a Drug field 66, a Size field 68 a Dosing field 70, a generic flag 72, an Expires field 74 and a Mine field 76, in which the various characteristics of patient Mary Harrington's previous prescriptions are listed.

Prescribing zone 44 comprises three active buttons, New Rx button 78, Send Rx button 80 and Close button 82, below which extends a prescribing header bar 84 which contains field identifiers for data entry of a full complement of prescription details. Available prescription detail fields comprise a Condition field 86, a Drug field 88, a Generic field 90, a Form field 92, a Size field 94, a Route field 96, an Amt (Amount) field 98, a Refill field 100, a Dosing field 102 and an Expires field 104.

Multiple lines of the selected patient's prescription history are listed in patient history zone 43 in the middle of the screen for convenient review by the physician-user, and possible renewal, with scrolling or paging of extensive histories. Depending upon the patient's previous whereabouts and service providers, individual lines may come from multiple remote sources. Such histories are preferably compiled by the host computer facility in response to a call from the user device (see the description of FIG. 16).

Prescribing zone 44, lower down prescription creation screen 39, allows a physician user to select and prescribe drugs and dosages, for the selected patient, in this case Mary Harrington, and to transmit the created prescription externally across a data network to other interested and authorized parties for prescription fulfillment, patient record updating and the like.

Select Patient button 46 returns to the patient selection screen of FIG. 2 for selecting a different patient from one or more lists. Preferably, Select Patient button 46 draws up a "Today's Patients" list or whichever patient list the user last selected from, or a default, user-selected patient list, and provides the options of selecting a new patient from alternative patient lists.

Problems button 50 brings up a patient problem history information screen such as that shown in FIG. 12 (to be described) in which a historical record of the patient's individual symptoms and diagnoses is listed and to which new problem reports can be posted. To maintain data integrity, and as a legal safeguard, historical information is not editable but may be supplemented, for example by reporting the subsequent status of a problem as (still) active or inactive. Preferably, any such additions to the record are stamped with the identity of the reporting physician, providing valuable elements of a treatment decision-making audit trail.

The patient's drug-related allergies, or drug reactions, are brought up in possibly editable form (screen not shown) by activating an Allergies button 48 and may be automatically system updated, if desired by adding newly reported drug reactions and allergies. Desired personal or drug records relevant to possible allergies of this patient may be summoned from the host computer facility, which may in turn call on the remote database data-retrieval network for records or record elements.

Rx History button 54, scrolls, drops down, or otherwise accesses any additional patient history lines beyond what will fit in prescription history zone 43 and may introduce vertical or horizontal scroll bars, or both, into zone 43, enabling the user to display any desired section of a patient's prescription history in zone 43 with the top line of the history highlighted. Any desired prior prescription line displayed in zone 43, can be highlighted by clicking or pressing on it.

A highlighted prior prescription can be automatically renewed by clicking or pushing an Renew Rx button 62. Typically, prescription creation screen 39 opens with the most recent prescription highlighted for possible renewal. Activating Renew Rx button 62 posts a highlighted prior prescription into prescribing zone 44 for automatic renewal, after editing, if desired. Renewal of any prior prescription can thus be effected in as few, as two user steps by pressing Renew Rx 62 to post a highlighted previous prescription to prescribing zone 44 and a single further action to complete a prescription from there. If desired option buttons such as Renew and Send Last Prescription or Renew All Active Prescriptions can be added. Pressing header buttons Condition 64, Drug 66, or Expires 74 causes the drug history display to be sorted by the selected header enabling the prescription history to be evaluated according to a particular parameter. This feature is of particular value for patients with long and complex treatment histories.

An important novel feature of the inventive prescription management system is the ability to associate a specific patient condition with each drug prescribed. By capturing detailed information on every prescription the system automatically builds a novel patient medical record having new uses in evaluating individual patient treatment and in enabling powerful new, multi-center outcome studies for evaluating therapies in various populations of patients.

By deploying the inventive system regionally, nationally or in some other population area, and employing the preferred methods for retrieving patient data from remote sources, as described herein, a complete patient record of all activity within a region can be built. Preferably this is a virtual patient record dynamically assembled only from original source data, which, as described above, is maintained in component form at multiple distributed source databases, is retrieved therefrom across a data-retrieval network from which the source databases can be accessed, and is compiled or assembled into a single virtual or transient record that appears to the user as an integral system data resource.

Outcome Studies, Prescription Cost Savings and Drug Alerts

Patient histories generated by the inventive system can show not only the drugs prescribed, but also the conditions for which they were prescribed, allergies, demographics, insurance coverage, treating health care providers, and so on. Known medical management systems do not provide listings associating each prescribed drug with a patient condition or problem, as reported to, or diagnosed by their physician.

Careful review of a patient's record for relationships between amelioration of problems and prescription of particular drugs can provide important information about the efficacy of a drug for a particular problem in a given patient. Review of a physician's prescribing record, detailing the various drugs selected to treat the different conditions exhibited by the patients encountered in the physician's daily practice, can reveal valuable information about the physician's prescribing practices and the degree to which they follow formulary guidelines.

This information is clearly of value to the individual physician and can, if desired, be enhanced by including in the problem record a condition severity rating, enabling declines (or increases) in severity to be reported. The resultant patient prescription history, replete with dated information as to patient problems, what drugs were prescribed to treat those problems, what forms, routes of administration and dosages were used and, by implication from the timing and nature of subsequent problems, what the outcome of that prescription was, provides a very attractive treatment evaluation tool to a physician, and a powerful inducement to any professionally conscientious physician to use the prescription management system of the invention.

Implementing the invention on a wider scale, valuable new outcome studies and clinical trials are easily, or even automatically, performed. One of many problems in successfully implementing the herein described prescription management system on a large scale is one of funding the system. Medical cost structures, with their reimbursement systems leave little scope for expenditure on aids to overall practice improvements which may have to be squeezed out of tight overhead budgets. Accordingly, significant cost to the physician user, or user's medical facility will be a major deterrent to system adoption. Preferably the system is provided to prescribing users on a low-cost or no-cost basis with funding from outside sources.

Implementation of the invention is expected dramatically to reduce the overall cost of prescriptions and this saving has been estimated to be from 20 to 40 percent of total prescription costs. Savings will accrue initially to the drug benefit management companies who reimburse the direct costs of most prescriptions, but can be expected eventually to be passed to corporations and consumers by way of lower drug benefit rates. Such savings realized on a national scale would amount to many billions of dollars and provide an avenue of reimbursement for system proprietors. In the early 1990's, the cost of prescription drug benefits is one of the fastest rising components of all health care costs.

Outcome studies produced by the system may have substantial value to various parties, and their sale can support system costs, as may formulary compliance savings. For example, drug efficacy data is of value to pharmaceutical companies, as is early warning data from reliable specialists regarding adverse reactions. Subject to confidentiality and other relevant controls, such data can be automatically compiled and readily supplied by system management, requiring only approval, not active participation by involved physician prescribers. Equally, the system may facilitate clinical trials by identifying health care providers or prescribers who would be likely participants in trials, based upon their having frequently diagnosed relevant conditions, or specified relevant drugs, as shown by their historical prescribing profiles, or relevant patient histories. Suitable patient pools can be identified similarly.

Organizations participating in outcome studies, for example health maintenance organizations, insurance companies, hospitals, physician alliances and the like, and may pool their data but may not wish to reveal certain proprietary data. By employing data access control methods for accessing such organizational data, such as the methods described in detail herein for controlling access to patient's rights, the system of this invention can enable organizations to control what data they release.

To implement such clinical trials, additional information required for collection can be obtained by flagging selected prescribers' profiles to trigger additional on-screen routines so that whenever a trial-related drug or condition is selected by the prescriber, they will be asked to supply necessary additional information. For example, whenever a prescriber participates in a trial relating to treatments for gastritis, the system can request information as to whether certain tests were performed, and what were the results of those tests. Thus, the test drug might be appropriate for, or be in trials relating to, gastritis testing positive to *H. pylori*, whereas a different drug would be indicated for *H. pylori*-negative gastritis.

The system can also provide, preferably from source databases, complete prescription drug disclosure requirements as set forth by the FDA, including full cautionary information, for example as is now set forth in the Physicians' Desk Reference (Medical Economics) and Physician's GenRx (Denniston Publishing) knowledge of which by the prescriber may be necessary to avoid malpractice liability, and dissemination of which may limit a drug manufacturer's liability. Efficient promulgation of drug disclosure information to system users is tantamount to publication, yet can be more current than any printed document, and may be accepted as an alternative to hard copy publication or supersede it.

In addition, the system provides a valuable means for government agencies and others to communicate important messages, such as drug warnings and alerts, quickly and directly to physician users. Electronic mail accessed via Mail button 16 can be used for this purpose, and may include priority flags triggering screen alerts, but a much more powerful route for communicating warnings relating to particular drugs is to associate the alert with system information on the drug so that when a user calls up the drug in question, they receive the warning or alert, or other special message.

In the extreme case of withdrawal of a drug from the market, that fact can immediately be communicated to system users. Thus a drug can be withdrawn from the market the same day by making a system entry preventing completion of a prescription for the withdrawn drug. Alternatively, a warning can be posted directly to the prescription. Current users of the medication can be identified from prescription history records, referencing not only drugs prescribed, but also prescription expiration dates. Both the patient and their doctor can be notified immediately. In this case, electronic mail is a preferred route for notifying the physician.

Relative cost-to-benefit data can also readily be prepared in outcome studies when individual drug costs are factored into the data, and such cost:benefit data can, in some circumstances have very substantial dollar value to drug benefits management companies whose objectives are to maximize the quality of care while minimizing the cost of that care.

Pharmaceutical and managed care companies can gain marketing benefits from use of the system to introduce new drugs or new uses of old drugs to physicians, in a relevant manner, at a moment of peak interest.

Other benefits can be derived from outcome studies using the novel drug-prescribed and condition-treated data records provided by the prescription management system of the invention. For example, the appearance of a new patient problem may be insignificant when associated with prior prescription of a particular drug for one patient, but may gain significance when repeated for a number of patients.

Optional system enhancements may enable post-introduction market surveillance of new drugs to be conducted for adverse outcomes to the treatment of a specified condition or conditions. For example the system may monitor patients reporting new problems after having been prescribed the new drug in question, refer such new problems to the physician user to qualify them for medical relevance and then statistically compare a collection of similar reports with data on a pool of similarly treated patients for significance.

Continuous post-market-introduction monitoring of a drug in relation to the treatment of conditions is possible, and an end-to-end solution to the problem of managing unanticipated problems arising with new drugs can be provided: the system provides a vehicle data collecting relevant data; parameters and a means for analysis of that data; and a means for disseminating alerts and advisories regarding newly discovered problems. The same vehicle is used for all three steps.

With such a system enhancement, one specialist pioneering a new drug for a particular condition may provide an early warning of adverse reactions not identified in clinical trials in a manner not heretofore obtainable, because of the difficulty of coordinating prescription and diagnostic data.

Quickly and conveniently presented at the point of care, as an integral part of the prescribing process, in the manner achieved by the system of the invention, this information can be of immense value to a physician when treating a patient, widening the physicians' choices beyond their own field of knowledge (by suggesting new drug information) and helping the physicians optimize the prescribing process.

Another advantage of the invention is that each physician user inherently and easily supplies critical enabling data for outcome studies as part of the prescribing process. No extra effort is required by the physician to make the data available for studies. One potential difficulty in making such studies is the existence of legal barriers to aggregating patient data into studies without specific patient permission. While this might be obtained on a piecemeal basis or by the prescribing physician, a much better solution is provided by centrally maintaining patient directed patient-record-access specifications, as described above. The system can then include only those records of patients agreeable to becoming study participants in such outcome studies.

The historical drug-prescribed and condition-treated records obtainable by using the invention can provide a basis for condition-based treatment guidelines developed by drug formularies. This novel data provides a new vehicle for outcome research for managed care, leading to new approaches to cost-effective prescription treatments.

Compilation of an extensive or national database of (patient-anonymous) records providing a statistical historical listing of drugs prescribed versus associated conditions for which they were prescribed would be in the public interest and of considerable value, so long as patient-confidentiality were maintained. Widespread adoption of the present invention can help achieve this desirable goal. It is relevant to note that FDA regulations only permit a drug to be promoted for approved, specific therapeutic purposes but physicians are professionally free to prescribe an approved drug for any condition for which they believe the drug to be effective or useful so that, failing specific point-of-care diagnostic information, no assumptions can be made as to the treatment objectives of any particular prescription. Accordingly, prior to the present invention, statistical prescribing data have generally lacked knowledge of why a physician prescribed a particular drug, and such data is, in most cases, not useful for outcome studies and cannot be related back to other patient-specific variables present in the patient's medical record.

Prescription History Record

Referring to the prescription history zone 43 of the FIG. 3 screen, under the Condition field 64 is listed a condition reported as active when the drug was prescribed. Drug field 66 may be a generic name or a brand name. The Size field 68 is the dosage size. Dosing field 70 shows the dosing frequency. The "G" flag 72 is for generic and is a simple yes/no indicator. An Expires field 74 displays an expiration date system calculated from the prescription quantity (not shown), the size and the dosing rate and indicates the day on which the prescription will run out.

The last column, Mine field 76, is a yes/no toggle flag indicating whether the prescribing physician was the current system-designated physician user ("Y"=my prescription) or some other physician ("N"). Another prescribing physician's details and other data relevant to a previous prescription can be obtained by pressing Rx Info button 60, or double-pressing or -clicking on the appropriate prescription history line, to draw down a prescription information screen, for example, as shown in FIG. 12. Additional available options, if any, can be accessed through the Rx options button 56.

Update button 58 can be a simple blinking indicator alerting the user that their device is communicating with the host computer facility and actively processing a local update. To indicate additional time taken accessing remote databases, the message can change to "Remote Retrieval", if desired. Additionally, Update button 58 can activate various update options, selectable from a menu., if desired. For example, Update button 58 may offer a selection of different sources from which to update the patient's prescription history. While a preferred objective of the invention is that the prescription management system obtain a comprehensive, nationwide update of any previous prescribing activity regarding this selected patient, considerations of system speed, system development or marketing considerations may make it desirable to offer patient prescription histories drawn from all prescribing activity in a more limited geographical region, for example, local or regional updates local network updates or capability to update from the physician's institutional or office practice information systems.

New Prescriptions

Activating the New Rx button 78 highlights the first available blank line in the lower portion of the prescription management screen for creation of a new prescription by a physician-user. During the prescription creation process, the user receives intelligent decision support from the system of the invention. Preferably, the system proffers the prescribing physician comprehensive relevant prescribing data to enable creation of a new prescription intelligently, in an informed, manner with routine look-up functions being fully automated so that professional time spent on routine chores is minimized or eliminated. To this end, data entries available via both Condition button 86 and Drug button 88 are selectable from extensive lists, as will be described hereinafter.

As described above, the system provides the user through their interface device and a linked host computer facility, transparently connectivity to multiple remote proprietary databases for retrieving necessary data such as drug and condition lists.

Pressing (or clicking on) highlighted fields beneath the headers in prescribing header bar 84, in most cases, activates pull-down menus, or data entry scrolls. Generic field 90 is merely a toggled flag while Expires field 104 is a system-calculated field. Although provision can be made for a physician to make original entries, the preferred embodiment provides a comprehensive selection of system-generated drug prescribing data from which the user may make selections.

If the user knows the drug they wish to prescribe, the drug name may be keyed in or, preferably selected by highlighting and clicking from one or more intelligently maintained lists presented in drop-down menus to post it to the respective highlighted field under Drug header 88. Alternatively, the user can select a condition from a condition list and make a drug selection appropriate to that condition from a drug selection screen such as those shown in FIGS. 4 through 11 as will shortly be described in more detail.

Generic flag 90 is a simple yes/no indicator which is linked to each drug selection to approve generic drug substitution for brand name drugs by the pharmacist, if such substitution is permitted by state regulation.

Prescription Quantification

The Form, Size, Route and Amounts headers 92-98 are linked to the drug selected and bring system resources to bear to enable a prescriber rapidly to quantify the prescription with appropriate dosages that can be filled at a pharmacy, without undue difficulty. Activating any one of the fields under headers 92-98 drops down a menu, which menus together offer a selection of all known formulations of the drug selected, as provided by the manufacturer, using comprehensive drug inventory data accessed via the host computer facility or its supporting data-retrieval networks.

The entry for Form field 92 may be selected from choices such as capsule, caplet, tablet, and liquid. That for Size field 94 might be a selection of 50 mg, 100 mg, and 200 mg and the Route field 96 selections might be "PO" for per oral, by mouth, "PR" per rectum, "IV" for intravenous, and so on. The displays are related and intelligently selected to display relevant options. Thus, for example, if "PO" is selected as the route of administration, only PO dosage forms are displayed. On the other hand, if PO oral forms are selected, "PO" appears as the route of administration.

The Amt field 98 is the amount or quantity of drug to be dispensed in the prescription, for example 30, 50 or 100 capsules or 50, 55, or 100 ml of liquid. Refill field 100 shows the number of times refilling is permitted and Dosing field 102 has two columns, one being a numeric designation of a number of tablets, caplets or liquid dosages to be taken at any one time and the other being an alpha indication of the dosing frequency such as QD for daily.

In an optional, modified embodiment of the invention (not shown), the system can calculate or suggest effective dosages for a selected drug, or a narrow range of effective dosages, according to dosage-relevant patient characteristics, for example, height, weight, age, sex, pregnancy and the like, taking into account the physical formulations in which the drug is known to be available. While these characteristics might be entered or selected from lists during the prescription quantification procedure, greater power is obtained by including them on the patient's record and having the system reference these characteristics each time a new drug is prescribed for that patient and make dosage recommendations according to the known behavior of the selected drug as it applies to the current patient.

Referring to the embodiment illustrated in the drawings, Expires field 104 can be system-calculated field from the entries in Amount field 98 and Dosing field 102, to indicate the day on which the last dose will be taken.

Alternatively, the physician-user can select, or enter, an expiration date in Expires field 104 for example to coincide with a desired duration of treatment, or next visit, the system can back-calculate refills or the amount dispensed.

Back-calculating prescription quantifiers is useful to coordinate multiple prescriptions to expire on the same day, for the patient's convenience and to reduce potential errors or abuses. Another valuable application of an expiration-controlled prescription is to benefit plan managers, enabling the physician, where appropriate, readily to coordinate prescription amounts to preferred schedules and programs of drug benefit plan managers, for example a ninety-day plan. Such preferred schedules can be system-offered or defaulted, if desired.

Alternatively, if desired, means can be provided for the physician themselves to write or key in the appropriate dosage entries for a selected drug.

In this preferred embodiment of prescription management system according to the invention, the drug and Condition fields 88 and 86 are linked together to express the therapeutic objective of the user's prescribing decisions, or the prescribing intent of the prescription, as will be described in more detail with reference to FIGS. 4 through 11.

As stated above, a preferred objective of the invention is to minimize need for keyed data entry, to minimize information look-up, or preferably to avoid all need for keying, by providing a comprehensive system interfacing with the user through easily operated data entry devices such as employed in pen-based computer devices. To achieve this end, the prescription management screen of FIG. 3, is preferably supported by comprehensive, fully adequate, up-to-date databases of drug information that, in a particularly preferred embodiment of the invention, provide a physician user with substantially all available relevant prescribing information on drugs, especially on those drugs they write most frequently, which may be favored with preferential device storage on the user's interface device, for rapid retrieval. Relevant prescribing information on other drugs, written less frequently, or not at all by that user is available on the network.

Prescription Fulfillment

When drug specification is completed to the physician's satisfaction, Send Rx button 80 is pressed to output the newly created electronic prescription in any desired form such as to print, to local or remote storage or to remote file transfer as an electronic prescription. The electronic prescription can be transmitted across a network for fulfillment by any specified pharmacy, for example, the patient's preferred pharmacy or a pharmacy preferred by the patient's drug benefit company for the particular patient's locality. Preferred routing options can be provided for the patient or the drug benefit plan, or both, and the system can default to appropriate options for the patient's benefit plan. Routing may be more or less complex and may for example split say a one-month prescription to provide a bridge prescription giving the patient an immediate one- or two-week supply from a local pharmacy, and sending the balance of the prescription for fulfillment by a lower cost mail order house. If desired, a Bridge Rx button (not shown) may be added to prescription creation screen 39 to perform such a prescription-splitting function.

Patient Compliance and Prescription Drug Abuse

Ensuring that a patient complies with the terms of a prescribed treatment, neither neglecting nor overindulging in a prescribed drug therapy, is a serious problem in health care management. It is difficult to ensure that out-patients actually ingest the prescribed amounts of medication at the prescribed intervals. Many mistakes and abuses occur. The problem is exacerbated when a patient is prescribed a confusing multiplicity of drugs that may have to be ingested in different amounts at different times of the day. The present invention enables, and includes, unique solutions to this problem that greatly facilitate a patient's ability to comply with a simple or complex regimen of dosages, without costly skilled supervision. In addition, many types of intentional abuse can be monitored and possibly prevented.

One approach to enhancing patient compliance, according to the invention, employs a novel dose-scheduling drug package that is readily adaptable to accommodating and scheduling single or multiple prescription dosages to help a patient take the right dose of the right drug at the right time, and will be described in detail hereinbelow.

Another approach is, to some extent, inherent in features of the prescription management system described herein. Where multiple physicians accessed by a patient utilize the system described herein, with common online access to, and assembly of, a patient's prescription history record whereby that record provides a current record of new prescriptions, then a common abuse can be controlled wherein a patient presents a problem or condition to more than one physician to obtain multiple prescriptions with a view to indulging in abusive ingestion or illicit resale. This problem is especially prevalent with analgesics. Where a physician, or perhaps pharmacist, if the patient's prescription history is available to the pharmacist, sees a similar current prior prescription has been issued, they can refuse to duplicate it.

Clearly, regulatory authorities wishing to control such abuses can further that goal by encouraging widespread, or universal, deployment of the prescription management system of the invention. Where the system also provides, for example in the patient's history record, notification from a pharmacy, or from a drug benefit plan linked to the pharmacy, of fulfillment of a prescription, and that information is available to the prescriber, for example from the patients' history record, another common abuse wherein a patient pleads loss of a prescription to obtain a duplicate, can also be prevented.

Bringing fulfillment information from the pharmacy to the point of care via the patient's record or other convenient reporting medium, with or without the intermediary of a drug benefit company linked as a remote source database, can provide not only a valuable prescription abuse monitoring parameter but can also be used to enhance compliance with the prescribed treatment, especially if coupled with an alerting system.

For example, the system may alert a prescriber that the intended expiration date of a critical prescription has passed without the prescription having been filled. The prescriber thus becomes aware that the patient has gone off the medication and can take steps to contact the patient and alert them to the dangers or problems that may arise. Alternatively, routine alerts can be passed to administrative personnel associated with the prescribing health care provider, notifying them of any unfilled prescription after a prespecified period of say two weeks or a month, or prescription expiration, or a shorter period for more critical medications.

Scheduled Dosage Drug Pack

Figure 15:
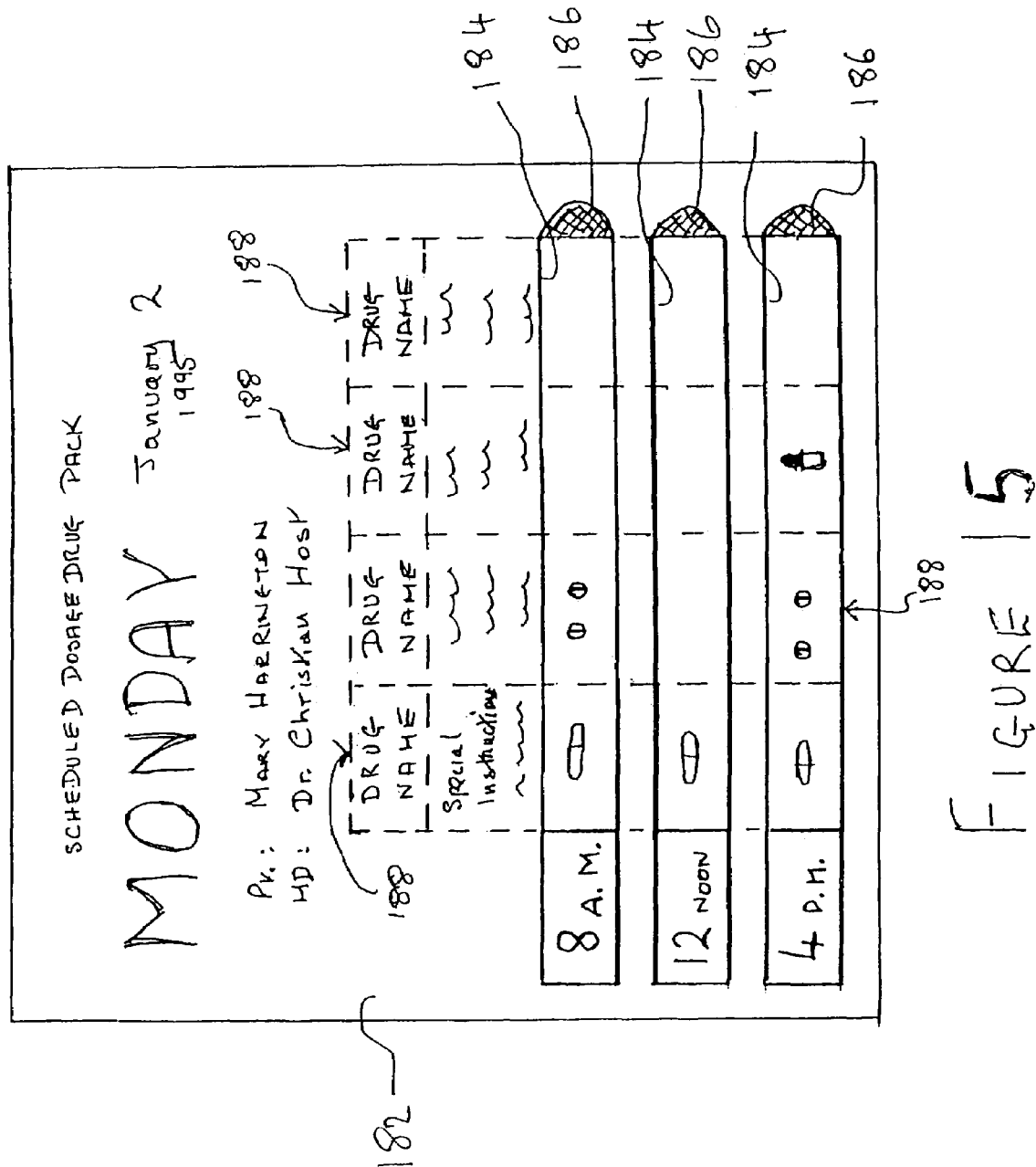
FIG. 15 illustrates a scheduled dosage drug package.

A particular benefit the system provides when a patient has multiple simultaneous prescriptions is an ability to print out a dosing schedule or better still, to generate a scheduled dosage multi-drug package from the electronic prescription, for example as shown in FIG. 15. Because the system knows dosage, dosage frequency and the duration of all prescriptions, it can report out what pills should be taken at different times of the day to comply with the requirements of multiple medications. The information used for such a further report can drive the dispensing of the drugs of a multi-drug prescription into a novel package which has multiple labeled or coded compartments for each of a number of dosing intervals.

FIG. 15 shows a scheduled dosage drug pack 182 configured as a daily pack with the day of the week prominent and the date, patient and doctor identified. Across pack 182 run three multi-compartment drug bays 184 each of which can accommodate up to four different solid drug formulations 184, pills, capsules, tablets, caplets, or the like and is sealed by a tear strip having an opening tab 186. Each bay is clearly labeled with a time of day at which the dosage in each bay 184 should be taken. Vertical zones 188 are dedicated to an individual drug and comprise a header with a drug name and special instructions (take with water, after food, and so on) and a compartment in each bay 184 for each dosage time. To demonstrate the flexibility and dose-organizing power of this novel, pack-based system a first drug is shown schematically in lefthand zone 188 with thrice-daily dosing, a second in left central zone 188 with twice-daily dosing and a third in right central zone 188 with once-a-day dosing. Righthand zone 188 is not used, but could be occupied by a fourth drug, the individual dosages of which are loaded into those individual compartments of Righthand zone 188 that correspond with desired dosage times or intervals.

Clearly, modified drug packs 182 embodying the principles of that shown in FIG. 15 could be configured for more (or fewer) doses or drugs or for different calendar periods, for example weekly or monthly packs rather than daily. Nor is the card configuration essential, for example, a multi-drug container could be in strip or roll or book form, or metal foil sheets, with tear or press-out compartments. Dosing errors are common with patients with multiple prescriptions, especially the elderly. There can for example be difficulty in knowing whether a dose has been taken or not. Drug pack 182 solves these problems in a simple inexpensive manner that is prescription controlled to organize multiple doses correctly and can be easily followed by most patients. Individual sealing of doses is hygienic and child- or overdose-resistant. Daily or weekly cards could be connected together by hinges to make compact concertina or book-like packs supplying a week or a month's prescribed drug requirements.

Variations on the theme of a scheduled dosage package will be apparent to those skilled in the art. If desired, the package could be standardized as to the number of dosage compartments, providing for example, a compartment for every hour, with those compartments lying between desired dosage times being obviously blank or never filled. A valuable feature of such packaging, which could be embodied in a single prescription package, is that by giving the physician-prescriber some physical control over the circumstances that exist when a patient is supplied with drug therapy for remote administration, the prescriber gains the freedom to adopt time-related dosage variations during the course of therapy, without confusing the patient. In a simple example, scheduled packaging might provide one pill in the morning, one at lunch time, and two at night, in an attempt to maintain blood drug levels through the night.

Other regimens could provide higher initial dosages to build up blood drug levels, followed by lower maintenance dosages. In any such case, the patient simply takes, or is administered, at any given time, whatever dosage or dosages have been packaged into the bay 184 that is appropriately identified by patient, time and date. More subtle or more complex regimens will be apparent to those skilled in the art, for example one drug might be discontinued, and possibly resumed after a suitable interval, while another continues. Another useful technique to be able to administer via the dosage-scheduling package described herein is to taper down one drug while beginning to administer another, to provide a graduated switchover. Changing anticonvulsant therapies from one drug to another is an example of where this technique may be useful.

Prescriber-controlled dosage scheduling can be included in the system via an additional window or screen, offering the prescriber selection of the relevant variables, such as time-related dosages, with defaults or preferred selections for what can be system-determined as the most probable or most beneficial choices for the patient being treated, or accord with the patient's formulary's preferences or with the particular prescriber's preferences, pursuant to the principles described herein. Specific tapering or starting protocols can easily be implemented for outpatients decreasing the requirement for costly skilled supervision.

Dosing Indicator Device

For more needy patients, the time- and date-scheduled drug packaging described herein can be rendered electronically or electro-optically readable, for example with bar-coding or by using transparent compartments, to cooperate with a novel dosing indicator device that a patient could take with them to their home or on their travels. Such a novel dosing indicator device, as contemplated herein, includes a time-and-date clock and is designed to receive at least one scheduled dosage package, as described herein, and to inspect that package to determine what drug pills, capsules or the like have been removed. In the event that a pill or the like is detected in any bay stamped with a date and time prior to the date and time clocked by the device, an audible or visual or remote alert, or a combined alert, is triggered. Inspection sensing is preferably electro-optical and targets individual compartments with a light beam that is reflected or diffused by an individual pill or associated light-modulating tag, or by a bar code stamp or label which is required to be removed with each dosage of any drug. The device can include a movable scanner that advances in relation to a package from one bay 184 to the next, scanning relevant compartments in the bay, as time passes, or it can comprise an array of photoelectric sensors registering with individual compartments of the package, which are electronically controlled and read in turn, as time passes. Equivalent sensing systems will be apparent to those skilled in the art.

A preferred embodiment of dosing indicator device accommodates, within an aesthetically pleasing housing, a multi-bay scheduled dosage package, a time-and-date clock, a time-related sensor to detect the presence of a drug dosage in the bays one or more alerting systems, associated electronics which may include a microprocessor, and a power supply, for example, a battery, ac connector or remote drawdown source, or the like.

Such a dosing indicator device can be embodied as a motor-driven single- or multi-drug dosage dispenser which, for example, can house a tape, or strip-like and preferably rolled, scheduled dosage package, having a time line along the roll, and advances individual bays 184 containing one or more dosages for a given dosage time, and presents a single bay 184 (containing one or more dosages) for external delivery and removal (for example by tearing) by the patient, or patient's aid, in timed relationship to the dosage time (a half hour before, perhaps) and triggers one or more alerts if the bay 184 is not removed (a half hour after, perhaps).

Preferably, each bay is accompanied by written information as to the patient, time and date, each drug, and any relevant dosing instructions. The individual compartments of such a removable bay cannot readily be sensed for the presence of individual pills clearly a sensor is required for the presence of an externally exposed bay. The system assumes that the pills in a removed bay will be ingested, but this assumption may be wrong on occasion. More rigorous patient compliance may be exacted by including in, or in association with the device, a receptacle for an emptied bay 184 and triggering alert means if such emptied bay is not received within a specified time interval. Emptied bays can be retained within the receptacle. To deter deceit of the receptacle it can read a time and date stamp, or other unique identifier on bay 184.

A multipatient version of the drug dosage dispenser described herein can also be provided for inpatient use in medical or health care facilities, especially hospitals and clinics. Such a multipatient version could comprise a central dispensing station, located for example at a nurse's station. The dispensing station can have multiple ports, preferably identified with bed locations and bed-occupants' names, whereby scheduled drug dosages for each bed-occupant patient are dispensed at scheduled dosage intervals, if desired with appropriate alerts or indicators. Nursing or other staff can readily remove and administer the correct drug dosages for multiple patients, possibly on a single round, or at specific times of the day.

Drug Contraindications

A further valuable feature of the novel prescription management system described herein is an ability to review a completed prescription for contraindications, or relative contraindications, such as patient allergies to the prescribed drug and such as possible drug-to-drug interactions with other drugs the patient has previously been prescribed. Contraindications may be clear-cut, for example, penicillin must not be selected for penicillin-allergic patients, whereas relative contraindications are less decisive and may be overridden by the prescriber in appropriate circumstances, for example an NSAID (non-steroidal anti-inflammatory drug) may be a preferred choice, in the prescriber's judgment for a patient with peptic ulcer disease, in spite of the attendant risk of ??

The system can also screen or review for other possible unintended adverse outcomes to the prescribed therapy, or for special precautions regarding a prescribed drug's use.

Preferably, the system alerts the physician-user at the point-of-care if they prescribe an offending agent, and provides an alert and an opportunity to amend the prescription before dispatching it for fulfillment. Processing to screen for interactions may occur on the user's point-of-care device or on the host computer facility or remote computer system, or may be delegated elsewhere by the host computer facility, and reported back to the physician, online as an integral function of the prescription process. Alternatively, interaction screening may be run on pharmacy-related systems, and notification of problems can be sent immediately to the user's point-of-care device using e-mail or using procedures within the prescription management application of the invention.

An allergies review can be conducted by checking system-stored known allergies of patient Mary Harrington against known pharmacokinetics and pharmacodynamics of the newly prescribed drug, entered in prescribing zone 44, for any of those allergies. Mary Harrington's allergy information is preferably an adjunct to her patient record and is downloaded to the user device from host computer facility when Mary Harrington is selected from the patient selection screen of FIG. 2. Drug allergenic proclivities are also downloaded from one or another remote database employing the host computer facility, under supervision of the inventive prescription management system, but preferably at a later point in the procedure, such as when a particular drug is selected for posting to prescribing zone 44.

Alternatively, the requisite information can be downloaded when the allergy review is conducted. Such allergy screening can alternatively be effected when a new drug is posted to Drug field 88. Either way, a positive system finding, indicating a risk of allergic reaction to the newly selected drug can activate a visual indicator or warning, for example, Allergies button 52 may blink and, if desired, an audible warning may sound alerting the physician to reconsider their selection. Alternatively, or additionally, an alert screen can tell the physician of an allergy if an attempt is made to prescribe an offending drug. Such alerts can be used to notify the physician of drug interactions, treatment warnings or can alert them to non-compliance with formulary recommendations, for example to the use of an unnecessarily expensive drug, and may be accompanied by suggestions for more appropriate alternative therapies.

Equivalent procedures can alert to possible drug interactions and contraindications, referring to the patient's prescription history for possible active or recently expired prescriptions that may interact with a newly prescribed drug, and for other patient data relevant to the drug's behavior in that patient. Alternatively, the such a review for possible undesired aspects of the drug's performance on the patient is made upon activating Send Rx button 80.

Electronic Prescription Transmission

Activation of Send Rx button 80 can provide a drop-down menu of choices including "Send this prescription" and "Add prescriptions prior to sending in a batch".

A preferred embodiment of the invention includes a capability whereby a completed prescription is transmitted across one or more data networks for fulfillment and record updating in a wired or more conveniently, for mobile professionals, a wireless broadcast. Preferably, where new information is generated in the prescription creation process, relevant remote source databases (which may be proprietary) are updated with appropriate components of the new information and such updates are effected with proper controls to ensure data integrity, confidentiality and authenticity. Using the system as described herein, all transactions generate an audit trail and are authorized or preauthorized by the patient.

Because of the currently substantial cost of air time, batch transmission is highly desirable. Accordingly, system defaults encourage the physician to elect batch transmission of multiple prescriptions for an individual patient, although in keeping with the principle of not imposing constraints on a physician, the system does not mandate such batch transmission. Executing a "Send Prescription" function outputs the prescription for fulfillment in any desired form, posts the completed new prescription to the prescription History zone 43 in the center of the screen, and outputs the new prescription from the user's station to update a control system or remote database, as desired. Prescriptions can be electronically transmitted to a pharmacy or pharmacy-management system for fulfillment, or printed on paper for paper-based fulfillment by hand delivery or fax.

The inventive prescription management system embodiment disclosed herein is designed flexibly to facilitate a physician's prescribing activities, to place helpful information at their fingertips and reduce manual look-up chores, while avoiding any authoritarian direction, mandate or constraint upon a physician's professional activities or judgement. Thus, while the system may attempt to provide intelligent options and exhaustive selection lists, options such as "other" are always available to permit the prescriber complete freedom of choice, whether or not their choice is known to system-available databases.

Optional system enhancements provide for enrichment of external communications, for example prescriptions and e-mail with what may be termed "electronic ink" messages generated at the user device. "Electronic ink" refers to notes or messages appended to external communications, or transactions in the form of free text or voice annotations for non-structured instructions, and the like. Voice annotation is particularly convenient, as well as possibly constituting unique user-identification and some currently available low form factor user devices incorporate a microphone, facilitating voice annotation.

Toward the end of prescribing flexibility, to avoid being second-guessed by physician users, and to command their respect and loyalty, the system should have access to, and provide to its users fully comprehensive drug and patient information so far as this is available. Comprehensive, accurate and complete drug and patient information are equally important for effective prescribing. It follows that the drug and patient information source databases from which the prescription management system draws, must be maintained up to date, by appropriate network services.

It is the normal, challenging nature of highly qualified professionals that those with the latest news, such as new drug releases and approvals, will want immediately to test the system for currency with the news.

The unique source-oriented information retrieval and updating system described herein provides preferred means for supporting the prescription management system of this invention with an adequate infra-structure of data-retrieval networks supplying a comprehensive array of up-to-date prescribing information and patient-related data to the point-of-care. Other suitable information data retrieval and updating systems will be apparent to those skilled in the art and can be linked to the system of the present invention to provide allergy and interaction alerts, formulary changes, new drug approvals, and to lock out or warn against, the prescribing of inappropriate or recalled drugs.

Drug and Condition Selection

Novel drug selection methods pursuant to the invention will now be described with reference to FIGS. 4 to 11. The condition list selection screen shown in FIG. 4 appears upon activation of Condition field 86 in the prescription management screen of FIG. 3, to enable a prescriber to approach selection of a treatment drug by first specifying a diagnosed condition. Alternatively, a drug may be directly specified by drug name by activating Drug field 88, as will be described in connection with FIG. 9, after which the prescriber selects a condition to specify the purpose of the therapy. Such condition or drug selection screens can be opened by similar condition or drug buttons in any other relevant screen or application, for instance in a patient encounter screen where the drug selection routines now to be described with reference to FIGS. 4 to 11 can be used to assist a physician to select or review treatment objectives in a computer-assisted patient encounter.

Condition List Selection

Figure 4:
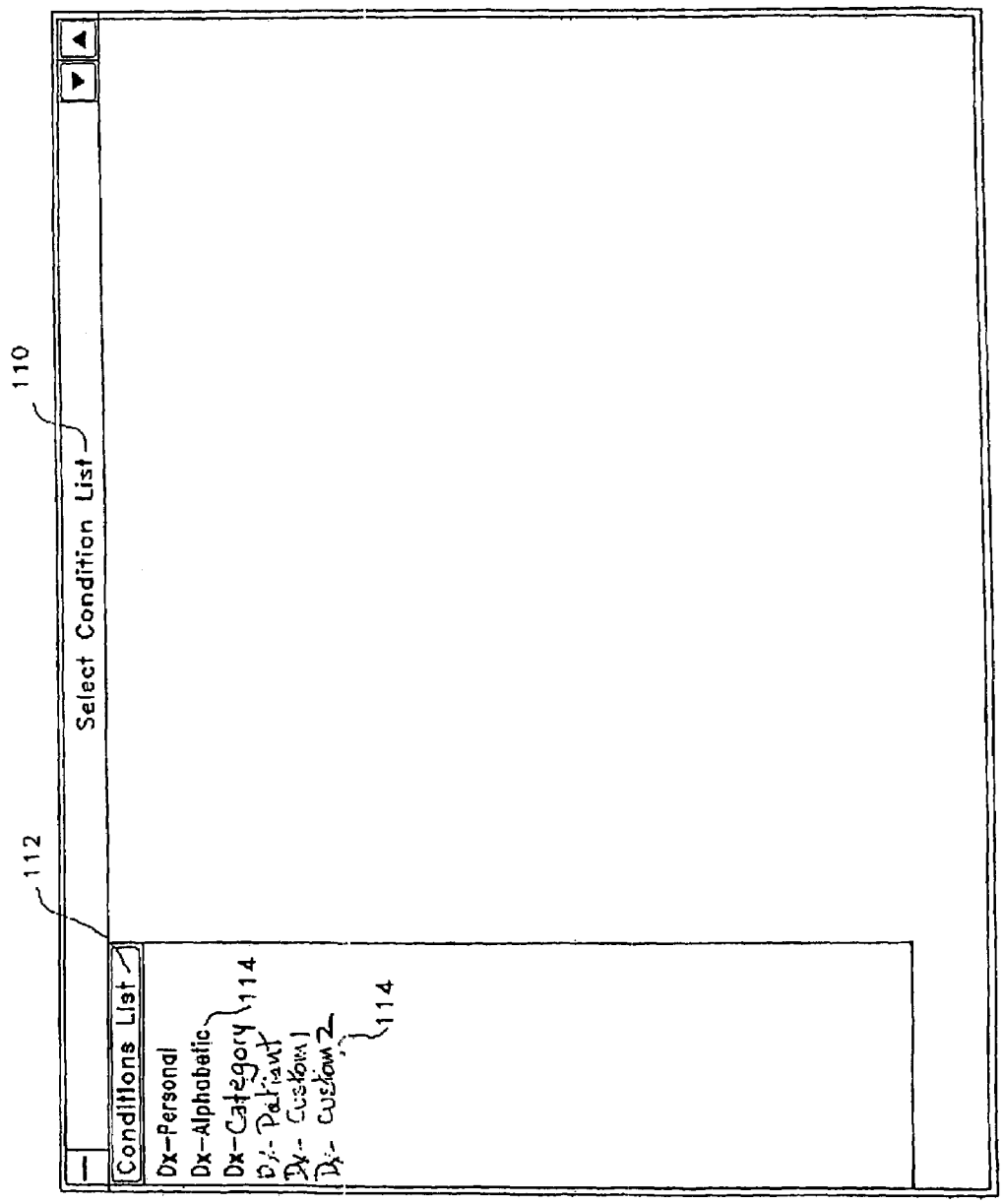
FIG. 4 is a condition list selection screen.

The condition list-selection screen of FIG. 4, provides a preliminary selection of a suitable condition list from which a physician user can work to select a drug. As shown, the screen comprises a Select Condition List title 110 and a Condition List display header 112 beneath which the names of Condition Lists 114 are grouped in a left-hand column. A right-hand column beneath header 112 displays the conditions 116 of whichever condition list 114 is highlighted, or otherwise selected. In this case the user's personal condition list 114 has been highlighted and may be seen to comprise a short list of commonly occurring problems that, for example, a general practitioner might encounter.

Multiple different Condition Lists 114 are available in this embodiment to provide a range of choices to physicians, and six are shown, by way of example. Three of these lists 114 classify conditions broadly by diagnosis (Dx) and comprise a system-maintained Dx-Personal list 114, an alphabetically organized Dx-Alphabetic list 114 of all conditions in the system and a Dx-Category list 114. Dx-Category list 114 lists conditions by broad therapeutic category such as cardiovascular, GI or dermatology. A fourth condition, problem or diagnosis list, Dx-Patient list 114 lists previously exhibited conditions or problems of the selected patient, in this case, Mary Harrington. Dx-Patient list 114 is system maintained (and manually supplementable) and changes according to the patient selected in the patient-selection screen of FIG. 2. Dx-Personal list 114 is also system maintained (and manually supplementable) and changes according to which prescriber signs on.

Preferably, the system includes frequency counters to track the conditions the user encounters with time, and the counts obtained are used automatically to maintain or generate a Dx-Personal list 114 for the user, which more closely portrays patterns of conditions encountered in the user's practice as time goes by. Base periods for reporting usage may be varied, or user selected, to list conditions encountered by frequency in, for example, the last year, the last five years, or perhaps, the last three months. Also, a default can be included to highlight a selected patient's last active condition or conditions as a first-line choice.

Preferably, any time a new diagnosis is made, the new condition encountered is placed in the user's Dx-Personal list 114 and any time a drug is chosen it is placed in a personal drug list for the user. The first time either a condition or a drug is selected, it is added to a user profile stored on the network, for example, at the host computer facility.

In addition, a physician-user can manually maintain one or more custom lists, Dx-Custom 1 list 114 and Dx-Custom 2 list 114, for their own preferred short lists of conditions being, for example, conditions appropriate to their specialty that the individual physician frequently encounters for treatment. Alternatively, libraries of specialty lists may be made available from which the user selects one or two lists for their personal use. Such custom lists 114 may be associated with different user activities, for example, Dx-Custom 1 could be used at a hospital where the user is an attending physician, while Dx-Custom 2 is used at a pain clinic where the user is a visiting physician. The various condition lists 114 provide alternative pathways to drug selection that a physician may use as an aid to deciding upon a course of treatment. Different pathways may suit different clinical circumstances or prescribers. Availability of alternative routes to relevant drugs may enable a physician to find improved treatments, and increase their range of choices, and may lead to new solutions to difficult prescribing situations.

The condition list selection screen shown in FIG. 4 is a gateway to other condition and drug selection screens. As an alternative for quicker selection, a preferred condition list (typically a Dx-Personal list 114) could be set as a default with other condition lists 114 being reached via a Change Condition List button (not shown).

Any or all condition lists 114 can be automatically supplemented or maintained by the system as it receives data in the course of processing numerous prescriptions for one or more physician users. In addition to supplementation with user-originating data, preferred embodiments maintain user profiles on a host computer facility which continually refreshes the data at the user's device so that the user can use any device or share a device with other users.

Condition Selection

Figure 5:
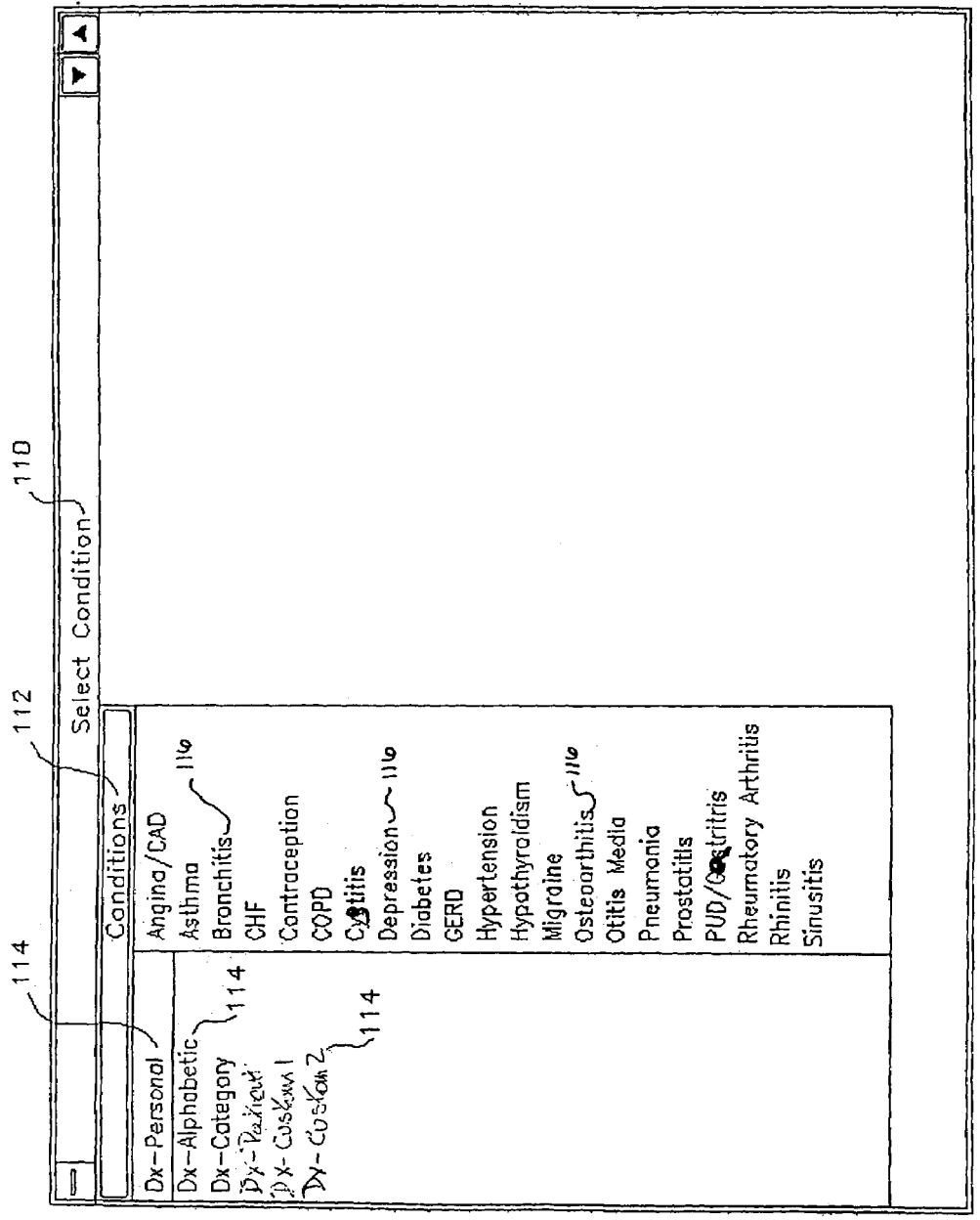
FIG. 5 is a condition selection screen.

In the Select Condition screen of FIG. 5, the patient condition 116 in the Dx Personal category shown comprise generalized groups of disease, some serious like diabetes and pneumonia, and others less so, for example rhinitis or sinusitis. More complex embodiments than the one shown here may categorize conditions into as many as four or five different columns of subcategories of condition according to disease pathology, therapy, personal knowledge and so on. Such condition categorization, as a preliminary to drug listing, provides a very powerful tool for physicians to view their prescribing options on screen and to organize them. Organization of drugs by lists of effectively treated patient conditions enables a user intelligently to access a large body of drug data selections. This approach provides multiple mapping so that the user can find a suitable drug or selection of drugs via different pathways according to their preferred work methods.

Different pathways to a drug via conditions organized in other ways, notably by body system, are illustrated in FIG. 8, described hereinbelow. Direct pathways of drug selection using drug lists are illustrated with reference to FIGS. 9 and 10, described hereinbelow.

In the example shown in FIG. 5, the user-physician has highlighted and selected a patient condition 116, namely, peptic ulcer disease (PUD)/gastritis, displaying, in the next right-hand column (see FIG. 6), a short, system-generated list of drugs known to be therapeutically indicated for PUD/Gastritis and which may be suitable for prescription or to have been prescribed in the past by that user for treating these conditions. The presence of the user's previously prescribed drugs, which may not necessarily appear on third parties' lists, helps personalize the list to the user.

Figure 6:
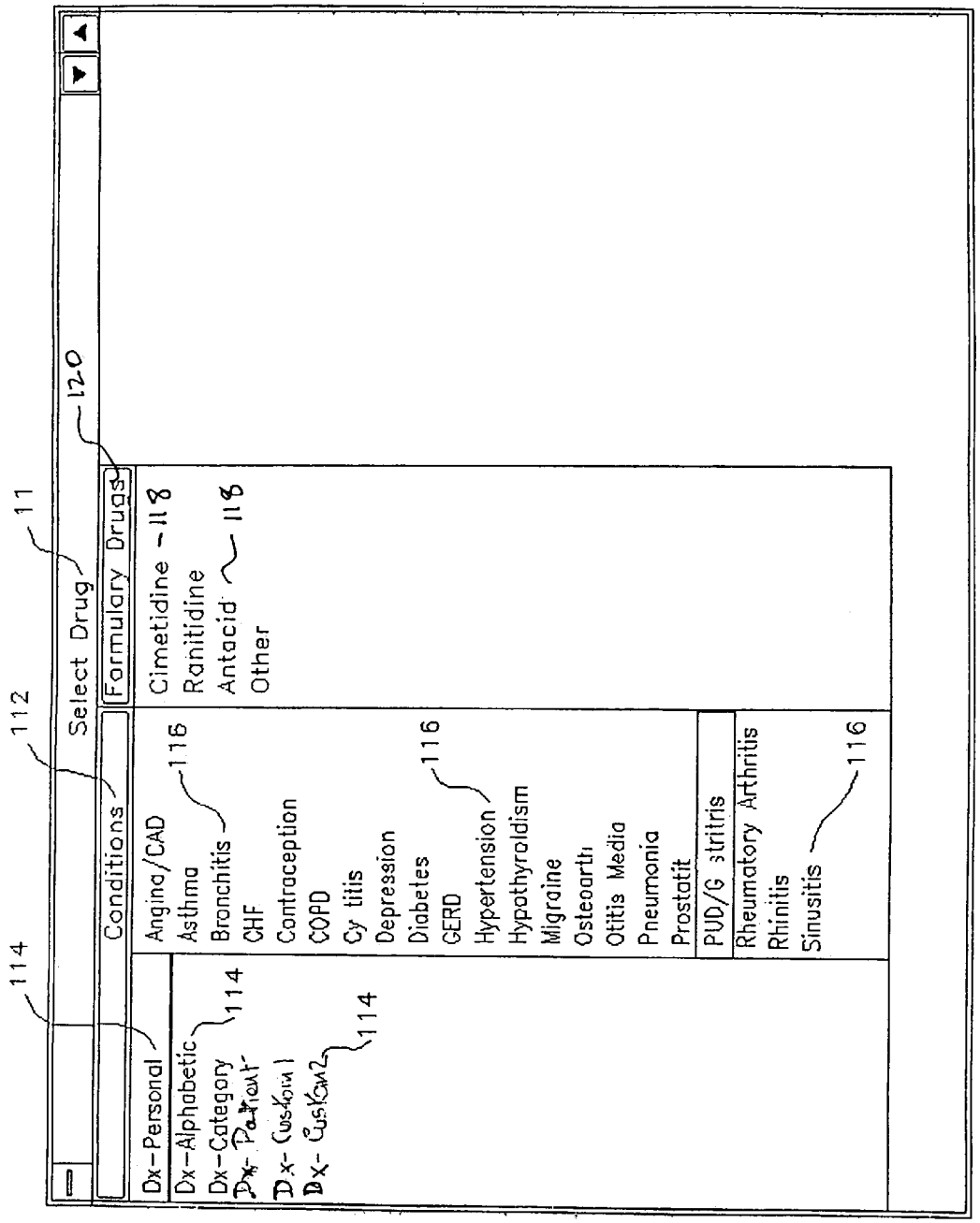
FIG. 6 is a drug selection screen, condition specified.

Referring to FIG. 6, now that a condition, PUD/Gastritis, has been selected, a new screen title, Select Drug 111, appears and selection of a drug to treat this condition proceeds. To aid the selection, a condition-specific, formulary drug list 118 is displayed in the next right-hand column of the Select Condition screen of FIG. 6 under Formulary Drug header 120. Alternatively, a physician's personal list of drugs may be displayed with formulary drugs highlighted. If desired, relative cost information can be included or alternative drugs may be ranked by preference of the formulary manager.

Formulary Drugs are those listed by a drug formulary specified by, or relevant to, the patient, in this case, Mary Harrington. The drug formulary may be generated by a prescription benefits management company and is a key ingredient in a system for reducing overall prescription costs by using volume purchasing to get preferred pricing on selected drugs.

A major problem in fulfilling the cost-control objectives of a managed care organization is that of informing a prescribing physician as to which drugs are in the formulary for a given patient. Noting that there are many different formularies it is quite impractical for the average physician to keep referencing different formularies for every patient every time they write a prescription. The aspect of the invention shown in FIGS. 6 through 11 helps solve this problem by providing computer access of remote databases containing the information and by presenting available formulary drugs in a form which is easy for a physician to use, reference and prescribe without enforcing physician compliance with a formulary's treatment guidelines and attempting to restrict a physician's exercise of their professional judgment.

To the contrary, the system of this invention is designed to empower a physician to make informed choices at the point of care. The system fosters quality, cost-effective prescribing. Physicians do not have to attempt to remember drug formularies and formularies may be changed with instant effect on all users without having physicians relearn the formulary. Where formulary information is called across a data-retrieval network, each time it is required, in accordance with preferred embodiments of the invention, from a remote source database, updates are automatically posted across the network.

Nonformulary drugs may be substantially more expensive than formulary drugs, or may not be covered by the patient's drug benefits plan, and may require out-of-pocket payments by the patient which circumstance may cause administrative problems to the physician and be a burden to the patient. Worse still, the patient may not have the prescription filled.

By including pharmacy-derived prescription fulfillment information, a patient prescription history can indicate whether a patient actually received a medication. The physician can be alerted (by e-mail) if a patient has not filled a prescription for a critical medication, for example LASIX (Hoechst), prescribed for hypertension, enabling a follow-up with the patient to be initiated.

Where formulary drugs are professionally acceptable to the physician and of equivalent therapeutic effect to non-formulary drugs, failure to use them is clearly undesirable. This problem is overcome by the present invention. If the physician is satisfied with the formulary drugs offered by the prescription management system of this embodiment, anyone may be selected and automatically posted to the novel prescription described herein as will be described.

Prescribing Non-Formulary Drugs

Should the physician know, for example, that cimetidine and ranitidine, drugs in a similar class, have been tried and found ineffective and that the condition is well beyond these first line treatments, so that none of the formulary drugs is suitable, then the physician can select Other, which selection displays a nonformulary drug list 122, under nonformulating drug header 124, as shown in FIG. 7. In this case, the physician selects Sucralfate as being a non-formulary drug in a different chemical category and having somewhat different therapeutic properties from those previously applied to treatment of this patient's symptoms.

Having made the decision to select Sucralfate, the physician is informed by the system display shown in FIG. 7 that sucralfate is a nonformulary drug not on patient Mary Harrington's prescription benefit management company's schedule. With this timely notification in hand, the doctor can, if appropriate, consult with a patient, explain the reasons for his or her drug selection and gain the patient's agreement to assuming the cost of the prescription, or obtain authorization from the plan to cover the cost of this prescription for this exceptional case. Physicians manifesting increasing compliance flowing from use of a prescription management system according to this invention can expect ready approval of a non-formulary drug on a justified exceptional basis.

By tying a diagnosed condition to a prescribed drug and requiring a condition to be recorded as a treatment objective before a prescription is fulfilled, new drug formularies can be created where prescribing of a drug is qualified according to the condition treated. For example, an expensive drug like captopril may be a first-line formulary choice for an acute condition such as congestive heart failure, but not a first-line choice, or may even be excluded as non-formulary, if prescribed for a chronic condition such as hypertension.

In practice, after the system learns the user's preferences, most condition and drug selections will be quickly made from the user's preferred or custom lists or from historically derived patient lists of previously encountered conditions, or previously prescribed drugs. The system adapts to the prescribing user to enable rapid creation of routine prescriptions. A minority of situations may call for less obvious therapies or therapies with which the physician has little or no experience. Physicians tend to be most reluctant to prescribe new drugs. Responsible physicians will usually scrutinize a great deal of relevant information before prescribing a drug for the first time. This effort is captured by the system which enables a prescriber to have quick access to their prior experience and confine their drug selections to drugs they have used previously and which were satisfactory. (A physician can of course edit their personal list to remove drugs that proved unsatisfactory for some reason or another, whether therapeutic or not, or they can be removed automatically based on decreasing frequency of use.)

In other circumstances a physician will need to select a drug with which they have little or no experience. Here, when it is most needed, the system provides major support and reassurance, presenting several different pathways to appropriate solutions enabling online access to the latest available scientific, clinical and commercial information about a new drug as well as screening for complications. The ability to offer drug detailing at the point of need for new drug information can be used to attract revenue from pharmaceutical companies, managed care companies or others, and is especially useful in decreasing the barriers to switching to first-time use of a drug. The system-provided prescribing information resources that are brought to the point of care are also valuable in enabling a physician to make quick therapeutic substitutions.

The drug selection screen shown in FIG. 8 offers, by way of example, one route to selecting a new drug not on the prescriber's short lists. Here, selection is condition driven and proceeds with the selection of a condition list 114, Dx by Body System or Dx by Therapeutic Class, and then locating a drug to treat that condition; or alternatively, by directly selecting a drug via drug lists 115 Rx by Therapeutic Class or Rx by Alpha. Displayed in FIG. 8, reading across the columns from left to right, are a list of body systems 117 from which the prescriber has selected Musculo-skeletal. In the next right column the system displays a list of conditions 116 that might be displayed by the musculo-skeletal system, of which nine are listed by way of illustration. From these nine the prescriber has selected Osteoarthritis. Osteoarthritis is posted to Condition field 86 in prescribing zone 44 of prescription creation screen 39 (FIG. 3).

With a condition specified, selection proceeds to the choosing of a drug to treat the condition of osteoarthritis. Drug selection proceeds through a preliminary selection of drug category, from a list of drug categories 119 in the next column to the right, enabling the prescriber to choose their therapeutic approach, in this case, as between employing an analgesic, a narcotic, a NSAID (non-steroidal anti-inflammatory drug) or a salicylate. A NSAID is chosen, generating an extensive list of drugs 121 in the right most column in FIG. 8, from which the prescriber can make their final selection which will be posted to Drug field 88 in the prescription creation screen 39 (FIG. 3).

The complexity of the prescribing process is graphically illustrated in FIG. 8. Even after narrowing the field down to a specific class of drugs, NSAIDS, for treating a particular symptom, osteoarthritis, there are still of the order of fifty drugs from which the prescriber makes a final selection.

Direct Drug Selection

Prescribers often know what drug they want to prescribe and will wish to access it very quickly, and may not use the system if they are unable to do so. This goal can be reached with user-adaptive personal drug lists organized to default to a prescriber's preferred choices, as described herein.

One preferred user-adaptive approach to providing a quick-prescribing pathway to a prescription is for the system to process the user's personal drug list, to highlight, or short-list or otherwise present those drugs on the personal list that are appropriate therapy for any of the patient's active conditions, and preferably also, that are on the patient's formulary.

Referring to FIG. 9, an alternative direct drug-specification pathway commences, reading from left to right, with selection of drug list 115 Rx by Therapeutic Class. From a list of perhaps fifty to one hundred drug categories 119 which appears in the next right hand column, the prescriber has picked Diuretics, generating an even longer list of diuretic drugs 121 from which the prescriber has picked Dyazide (trademark, Smith Kline Beecham). The system now calls for entry of a condition, in this case "hypertension". The extent of the lists of drug categories 119 and diuretics 121, again illustrates the bewildering array of drug selections with which a prescriber is confronted. An otherwise uncertain or overly conservative decision-making process can be rendered efficient, reliable and manageable by a prescription management system according to the invention.

The selection program illustrated in FIG. 10 provides a variety of pathways for direct drug selection via five drug lists 115, a personal, an alphabetic, a category list and two custom lists, analogous to condition lists 114. Here the user has selected Rx-Alphabetic list 115 and the system has displayed a portion of a long, scrollable list of drugs 121 in the next column. This approach can quickly locate a target drug when the physician knows it by name. Here Cefixime has been selected and the system calls for, and requires, the prescriber to enter a condition before proceeding to quantification of the prescription. In the next column the system lists conditions that the user has previously treated with Cefixime, highlighting the most recent condition so treated, or the system may display a previous condition of this patient that was treated with cefixime, not necessarily by the current user. If the physician wishes to attack some other condition with cefixime, such other condition may be selected from the last righthand column, activated by "other".

The diversity of conditions treatable with cefixime illustrates the potential for outcome studies based upon widespread use of systems according to the invention to refine definitions of the therapeutic scope of individual therapeutic agents by collecting data on effective new applications and on precautions, interactions and side effects.

Some Advantages of Condition-Specified Drug Prescribing

Being abundantly served at the point of care with relevant prescribing information at the critical moment of decision, the physician can eliminate many subsequent problems or difficulties which may lead to unnecessary paperwork, or surprised, annoyed or non-compliant patients, and to unnecessary phone calls between pharmacist and physician when a patient learns only at the pharmacy that their prescription is non-formulary. The system can eliminate much unnecessary "phone tag" between pharmacies and physicians. Improved physician and patient compliance with preferred guidelines will reduce the cost of care and increase the quality of care.

The availability, by means of the invention, of vital drug selection information, categorized by therapeutic condition and denoted as formulary or not, for the patient in question, rapidly assembled, preferably from remote source data, and conveniently presented to a physician for flexible use in their own personal work flow, greatly enhances prescribing practices, fosters cost containment and eases the administrative burdens that fall on heavily prescribing physicians. It enables informed choice at the point of care leading to a decrease in adverse outcomes of therapeutic choices.

Naturally the prescription management system of the invention can provide a variety of printed reports and other data outputs of any facet of the described operations. In some cases, these reports can be enhanced to provide entirely new products for example a dosing schedule such as that described with reference to FIG. 15, and shipping schedules or split prescriptions divided according to suppliers requirements.

Current and historical reports can, subject to the access controls described herein, be patient-specific, prescriber-specific or organization-specific and can be aggregated across various groups, pools, geographical regions, conditions, drugs, or time periods or combinations of any of the foregoing to provide a valuable data resource to health care providers, patients, managed care organizations, government agencies and others.

Further to enhance the prescribing decision process, additional features can be included on screens such as FIG. 7, for example drug pricing information, employing actual wholesale or retail pricing, or comparative pricing or on another manner of drug pricing or grouping, such as a comparative scale or price rating system, or relative pricing based on actual prescription benefit management company contracts. Such pricing information can greatly influence M.D. decision-making, improving formulary compliance and reducing overall drug costs, without restricting a physician's choices.

Figure 11:
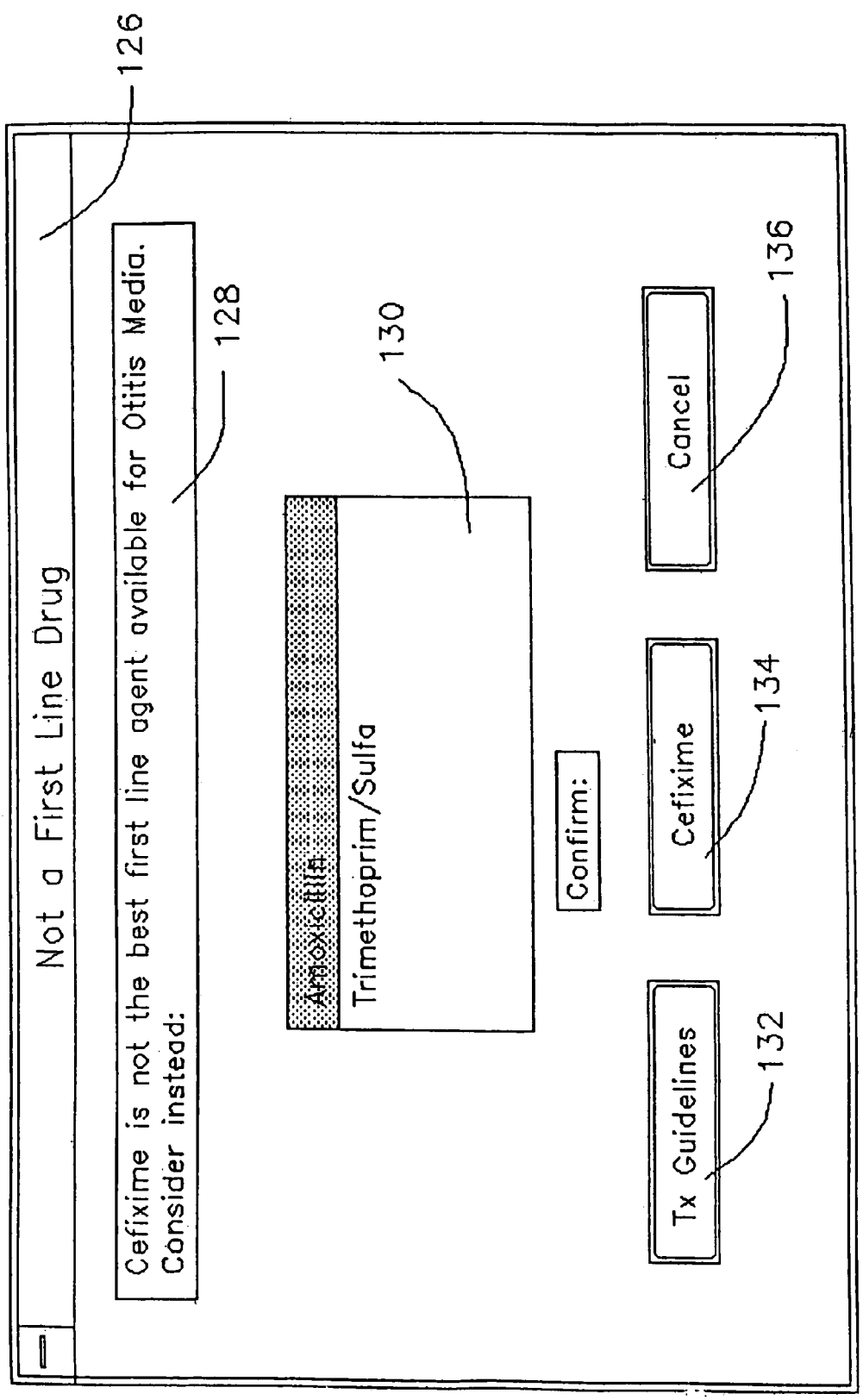
FIG. 11 is a drug selection evaluation screen.
Figure 17:
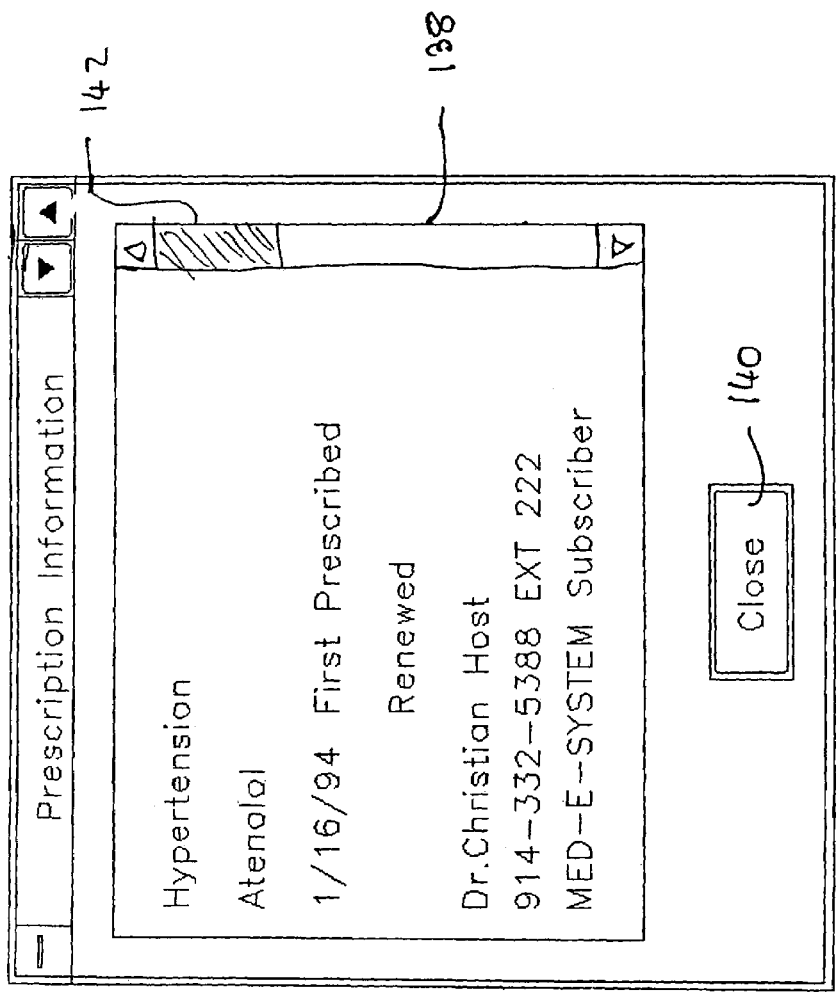

A powerful optional feature of the invention is shown in exemplary fashion by the drug evaluation screen depicted in FIG. 11. After a physician selects a drug from one of the screens of FIGS. 7 to 10, the system can optionally scan a drug preference database of preferred drug treatment for an evaluation of the merits of the selected drug in treating the condition. The drug preference database may be remote and may be maintained, for example, by a managed care organization, HMO, or prescription benefits management company. As the FIG. 11 example shows (which example employs different condition and drug selections from those used in FIGS. 6 and 7) one possible result of the database scan may be an on-screen report with an alert message, in header 126 advising the physician that the selected drug is "Not a first line drug" for treating the selected condition. As a helpful suggestion to the physician the system can also offer alternative drugs, from listings in the drug preference database, as being more meritorious for the treatment of the condition in question (pursuant to the maintaining benefit company's standards or, preferably, to objective literature reports).

To this end, the drug selection evaluation screen of FIG. 11 comprises an explanatory box 128 elucidating header 126; an alternative drug selection menu 130; and at the bottom of the screen, three action buttons; for example, Tx Guidelines 132 to access treatment information about the alternative drug highlighted in menu 130; a confirm button 134 to post the physician's original drug selection, in this case "Cefixime" and to return to prescription creation screen 39; and a cancel button 136 which returns the user to the drug-selection of FIG. 7.

The treatment information available via Tx Guidelines button 132 may include a literature reference supporting the system's finding that Cefixime is not a preferred first line agent for treatment of the selected condition, otitis media. Optionally there may be a selection on a drop-down menu from the Tx Guidelines button 132 enabling a physician, without further effort to have a copy of such a study sent to them. In a further optional embodiment, Tx Guidelines button 132 can provide the user with an access point to full disclosure and prescribing information on the drug. Available treatment guidelines information can include details of the particular conditions for which a system suggested alternative drug has been found effective, adverse conditions, preferred dosages and administration routes, literature sources and so on. This aspect of the inventive system provides a simple, nonintrusive technique for bringing new drug information to physicians at a critical moment of need, when creating a prescription.

Although described as a self-contained system, it will be appreciated that functions such as the identification and listing of drugs via conditions treated, and patient prescription histories will have value in other systems, for example, patient encounter management systems, and may be accessed directly from such systems via a prescribing information button.

As well as compensating for error or lack of information on the physician-user's part, the prescription review system exemplified in FIG. 11 has great value as an educational tool. Physicians can be subtly trained to improve their drug selection behavior. By using the system aggressively and exploring its information resources, as they are encouraged to do by the system's prompts and alerts, physician prescribers effectively receive education and training at the point of care. Improvements in drug therapy are subtle and complex and it is often difficult, even for the most conscientious of physicians, to be abreast of developments in any more than one narrow field of medicine. It is just as difficult for purveyors of new drugs to break in to a physician's packed work schedule to educate them as to the merits of a valuable new drug.

More than one alternative drug may be offered. Also in an optional embodiment not shown, the physician user may choose to display a screen of drug information regarding the alternative drug or any other drug. After confirming a drug selection the system can review the patient's history in relation to the selected drug and alert the physician to any relevant allergies, one-on-one drug interactions or, if appropriate, multiple drug interactions.

Often, when new drug information is presented, a physician is unable to consider it, yet when the information is needed, or could be used, for example at the point-of-care, when creating a prescription, valuable new drug information may be unavailable or forgotten. This invention solves that problem by presenting new drug information in a timely manner at the moment when it is most needed and a physician is most interested in considering it, namely at the time of writing a prescription. It gives a benefit management company the opportunity to influence a physician's choice at the most influential moment, during the prescribing decision.

User-Adaptive Drug Formulary Compliance

Conventional formulary guidelines specify one or more substantial lists of preferred drug therapies. Many of these drugs will be unfamiliar to most prescribers who will therefore be reluctant to prescribe them. Natural professional prudence makes most physicians extremely cautious about specifying powerful agents for therapeutic goals when they have little or no prior experience with the agents but will be responsible for the outcome of the treatment.

The system of the invention can provide a novel approach to drug formulary management whereby prescriber-centric formularies can be established. By means of the system, drug formulary guidelines effectively adapt to the user's prescribing patterns or can be followed effortlessly by the prescriber. This desirable prescriber-centricity can be obtained by giving priority to the prescriber's personal or custom lists or, better still if they are a subset of these, to the patient's history lists, and system-identifying patient-formulary preferences on those lists for easy final picking by the prescriber. Where the prescriber is selecting a drug providing effective therapy for a just-specified condition, the above procedure may often clearly identify a single drug meeting all requirements or may result in a short list of a very small number of drugs for final selection. Where no drug is listed as meeting all requirements, the system may so alert the user and suggest formulary drugs not on the doctor-specific lists or ask the user whether they wish to review appropriate non-formulary drugs from their personal or custom lists.

Patient's Prescription History

FIG. 12 shows a prior prescription information screen which can be displayed by double clicking the prescription display line or activating RX History button 54 in a screen zone such as prescription history zone 43 of prescription creation screen 39 shown in FIG. 3. The embodiment of screen shown in FIG. 12 provides a simple passive information display, comprising an information box 138, a close button 140 and a scroll bar 142 for scrolling or browsing a library of prescription histories. The displayed prior prescription information in box 138 comprises, for the selected prescription, the condition for which the drug was prescribed, the drug name, date of prescription, dates of any renewals and the name, phone number and any other appropriate identification of the prescribing physician, in this case it is the user physician, and any other useful details that may not be strictly prescribing information, including appended free text, voice annotations or other electronic ink. Where an "N" indication appears in the Mine column 76 on the prescription history line in FIG. 3, the name of another physician who authored the relevant prescription will appear in FIG. 12.

In addition to conveniently presenting useful historical prescription-related details, powerful optional features, for example, direct E-Mail communication with the physician whose name is displayed (or with some other physician) can be activated from the prescription information screen of FIG. 12 or other suitable screen, can be included in the prescription management system of the invention. Such options enable physicians to send an inquiry to, and perhaps retrieve relevant records directly from another physician such as a previous prescriber to the patient, or a referring physician. The invention facilitates the execution of such information transports during the user-physician's encounter with their patient. The screen of FIG. 12 could additionally have an Auto Dial button and be linked to other modes of communication to facilitate a direct connection to the physician of interest. Additional options include a display of historical dosage information and an ability to page through all prior prescriptions or all prescriptions for a given patient, a given prescriber, a given condition, a given therapeutic class, and so on, recapping some of the functionality of the FIG. 3 prescription creation screen 39.

Figure 13:
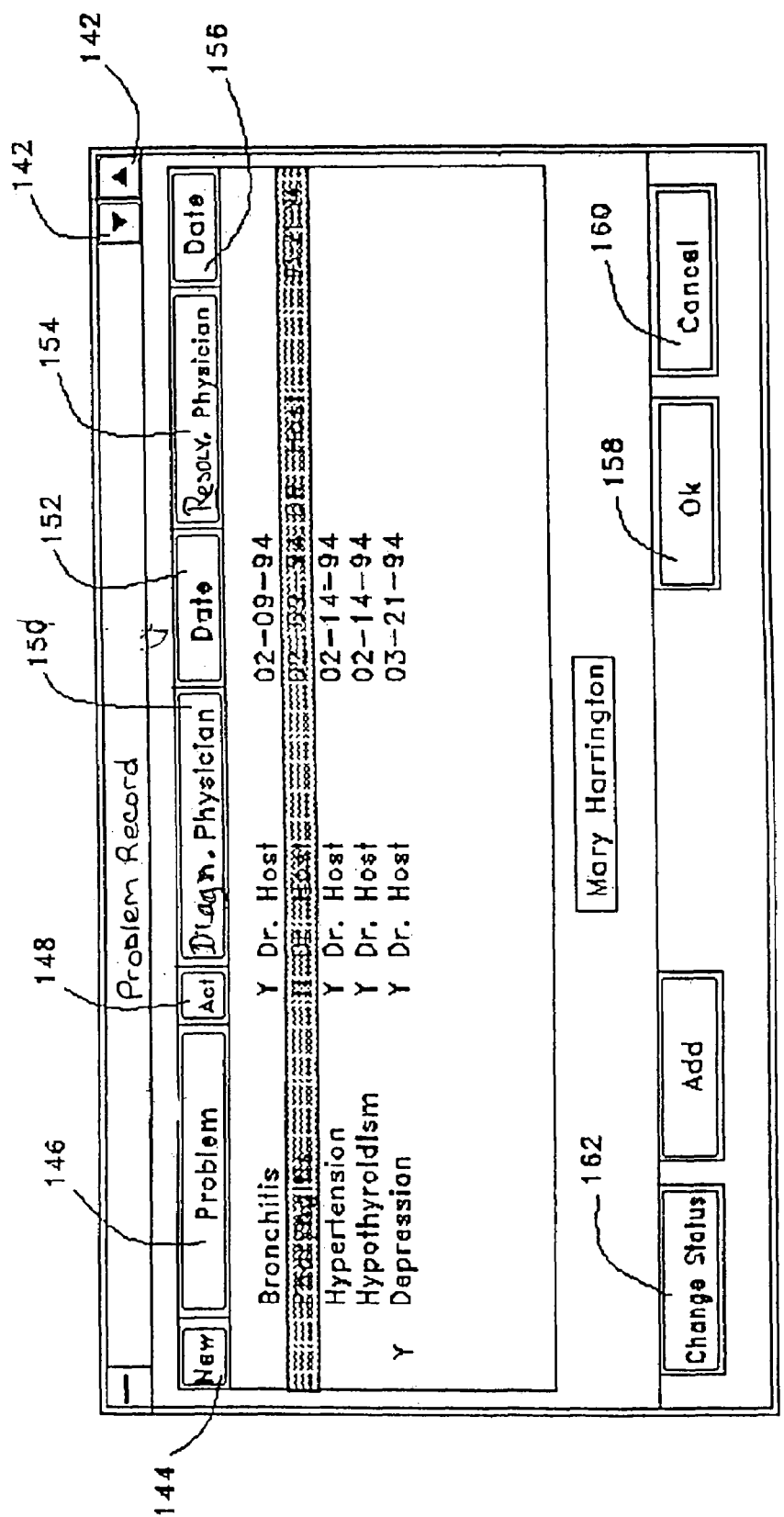
FIG. 13 is a patient problem history information screen.

A further optional feature of the invention is shown in the patient problem or condition screen of FIG. 13, openable, for example, from Problem button 50, FIG. 3, which tracks, as indicated by the field headers 144-156 extending across the screen, a history of the patient's problems and records diagnostic determinations regarding individual problems, in particular, the system captures information regarding the date when a new problem first becomes active and when it is "deactivated". These dates are associated with the name of a physician user, and thence with a patient encounter and can be regarded as authentic diagnostic determinations capable of being substantiated from the physician's office records. Additional information screens, detailing, for example laboratory or other diagnostic data, or relevant personal patient characteristics, for example height and weight, can be linked to problems as they are with drugs.

By processing such reliable base data, combined with historical prescription data associating a patient problem, or treatment category, or treatment objective, with a prescribed drug routine, valuable new information and outcome studies can be generated. For example, the duration of problems in relation to particular treatments can easily be calculated.

Using the FIG. 13 screen the system user, or the system, labels a problem or condition as new in New field 144; describes the nature of the problem in Problem field 146 from a condition list (not shown) such as condition list 114 shown in FIG. 4; selects a "Y" or "N" flag in Act field 148 to show the status of the condition as active or not; inserts the name of the physician adding the problem to the list in Diagnosing Physician field 150 (which the system will default to the current user); inserts the date the problem was added in Date field 152; inserts the name of the physician determining the problem is resolved or no longer active in Resolving Physician field 154; and inserts the date of resolution in Date field 156. Thus changes to the patient record are stamped with the name and date of the responsible physician to provide an audit trail. A physician identifier can be added if desired.

Problems that no longer manifest themselves to the patient or physician can be indicated as not active in Act field 148. The problem list can be sorted by header selection and preferably presents active problems at the top of the list by default.

Such a system-maintained problem list provides an easy and convenient reference to the patient's history of conditions or problems and of the duration and currency of such problems and constitutes a valuable case management tool for physicians. The problem list is automatically supplemented during the prescribing process with the latest prescriber's latest observations and diagnoses, as indicated by selection of one or more conditions for posting to a new prescription.

Where a patient complains of an old problem a quick prescription creation routine comprises selecting the problem from the Dx-Patient list 114, then selecting a drug from a system-generated pick list of drugs providing appropriate therapy for that condition. The pick list is preferably drawn from the doctor's personal list and is either compliant with the patient's formulary guidelines or indicates those guidelines, for example by inverse video, highlighting or the like, and also includes a selection of "other" to access drugs not on the prescriber's personal list. Such a quick prescription routine enables the most routine situations to be promptly handled, yet permits the physician to expand their prescribing horizons and does not merely require selection of the same drug as was used previously. Quick treatment substitutions are made possible by the system's presentation of available alternative therapies enabling the prescriber easily to see what alternatives are available and to explore those with which they are unfamiliar.

Also the problems or conditions on this list can be automatically posted to a patient problem list 114 to appear as an additional "Dx" list in screens such as those shown in FIGS. 4-10, to provide quick selection or review of a patient's historical conditions. Preferably, such a Dx-Patient list 114 changes automatically when another patient is selected.

As various system-using physicians, laboratories and the like encounter the patient or provide services to the patient, they become original sources for new record elements memorializing their encounter with the patient or the patient's attributes. The patient's history accumulates, and the system compiles, on demand, a cumulative virtual patient record including all newly created record elements. This current patient history record is promptly available to any authorized physician user on the network. In an ideal world, all relevant encounters are captured so that the patient's record is comprehensive or complete.

The value to a patient's care givers, of an instantly available, comprehensive patient record cumulatively reflecting all current and recent medications and conditions, is immense. Its availability to emergency personnel may be life saving.

The problem list screen of FIG. 13 is accessed from prescription creation screen 39 (FIG. 3) by pressing button 50. Selecting an OK button 158 or Cancel button 160, the problem list returns to prescription creation screen 39 (FIG. 3). Change Status button toggles the highlighted Act entry between "Y" and "N", and records a date and physician name with any status change. Add button 164 enables a physician user to add a new condition to the list, using condition selection pick lists, as previously described. This routine may be used to note problems for which there is no specific prescription given, e.g. obesity or senile dementia.

Where the inventive prescription management system is applied to statistical data collection for outcome studies, it is preferable to supplement the patient record with a range of relevant personnel data, to the extent that this is available, for example drug abuse behavior, smoking and habitual eating or drinking behavior, dietary habits, marital and family status, pregnancies, ethnicity, environmental factors, and so on. The system provides an excellent means for tracking these factors and their changes as they may pertain to an individual's health. For example, data fields could be added to record any of the foregoing data and the data could be updated by medical or administrative personnel in preparation for a patient-physician encounter.

Of particular significance to outcome studies will be death certificate information, and preferably this information is added to the patient problem record of FIG. 13, as appropriate.

More complex embodiments of the invention can integrate applications for prescription management with equivalent applications for diagnostic tests, laboratory analyses, and radiological studies to provide a more comprehensive patient history viewable in multiple screens. Of particular value in such an integrated presentation are laboratory results providing drug dosing levels, renal and liver function tests that provide important indications as to appropriate dosing, and so on.

Figure 14:
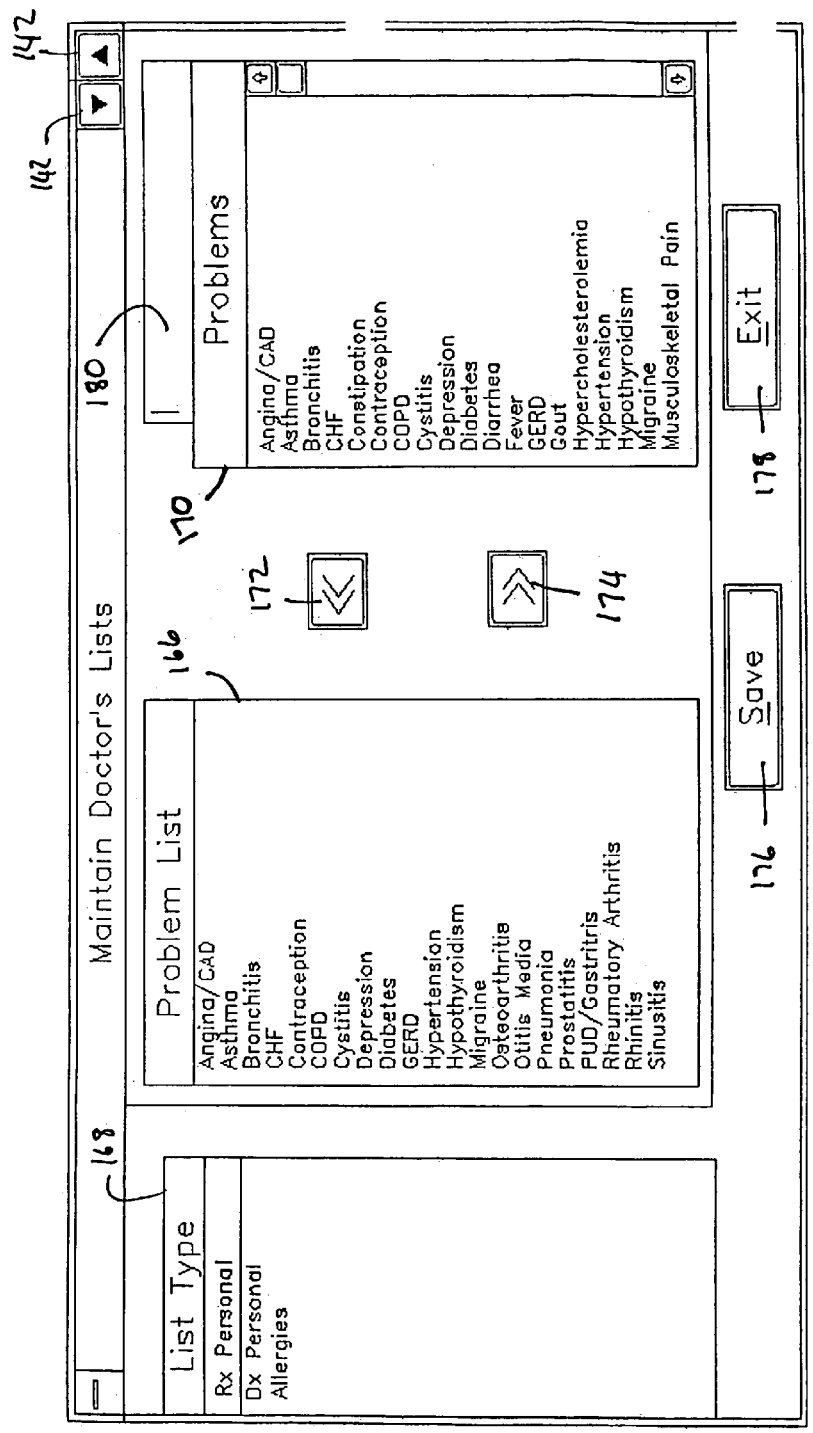
FIG. 14 is a manually updatable problem list maintenance screen.

FIG. 14 shows a manually maintainable problem record maintenance screen, for physician use, which can be accessed for example from the Doctor's lists button 24 in the system entry screen of FIG. 1. This screen enables a doctor or physician manually to maintain their own personal customized prescription, diagnosis, allergy or other useful lists, to supplement the automatically maintained system lists. If desired, problems the doctor's patients have experienced previously can be system-added to the list, for example when a patient is selected. These personalized lists or profiles are posted to the network where the system can retrieve them to any user interface device via a host computer facility, subject to appropriate password protection or the like. Relying upon such centrally stored personalized profile files, the system can present a customized, personal appearance, with familiar configurations, attuned to the user's work habits, at any geographical location from which the network can be accessed.

The problem record maintenance screen of FIG. 14 comprises a Problem List box 166, a List Type box 168 and a Problems box 170 displaying a comprehensive, or preferably exhaustive list of problems which can be selected and transferred to the network and the physician's problem list by pressing update button 172. Highlighted entries can be removed from the Problem List 166 by pressing delete button 174. Save button 176 and Exit button 178 perform the usual functions, and preferably provide options to cancel changes, and the like. Data entry box 180 permits an unlisted condition to be keyed in, or otherwise entered character-by-character and paging buttons 142 move between lists.

Archiving

Given the medical, commercial and legal significance of the transactions executed and the data generated by use of the system of the invention described herein, as well as the value of that information to the patient, the physician and many other organizations, maintenance of accurate historical records, or archiving, is desirable, or essential, and preferred embodiments of the invention provide archiving at a host computer facility 106.

Data storage burdens attendant upon long-term archiving are substantially relieved by using virtual patient records, as described herein. Pursuant to the principles relating to the use of virtual patient records dynamically created from source data record elements, the invention prefers to archive such data as will enable a full and accurate record of the past to be regenerated from diverse sources, rather than recording the past verbatim. Date and time stamped record elements allow recreation of a virtual patient record at any point in time.

Preferably, the data logged into archives comprise all data relevant to a patient's diagnosis and therapies, data relevant to the user's prescribing activities, including the prescriber's relevant electronic communications ("e-mail") with third parties (pharmacies, laboratories, other health care providers, or potential providers, to the patient, and so on) and access audit data as to parties accessing the patient's or prescriber's personal data.

System-Support Infrastructure

Figure 16:
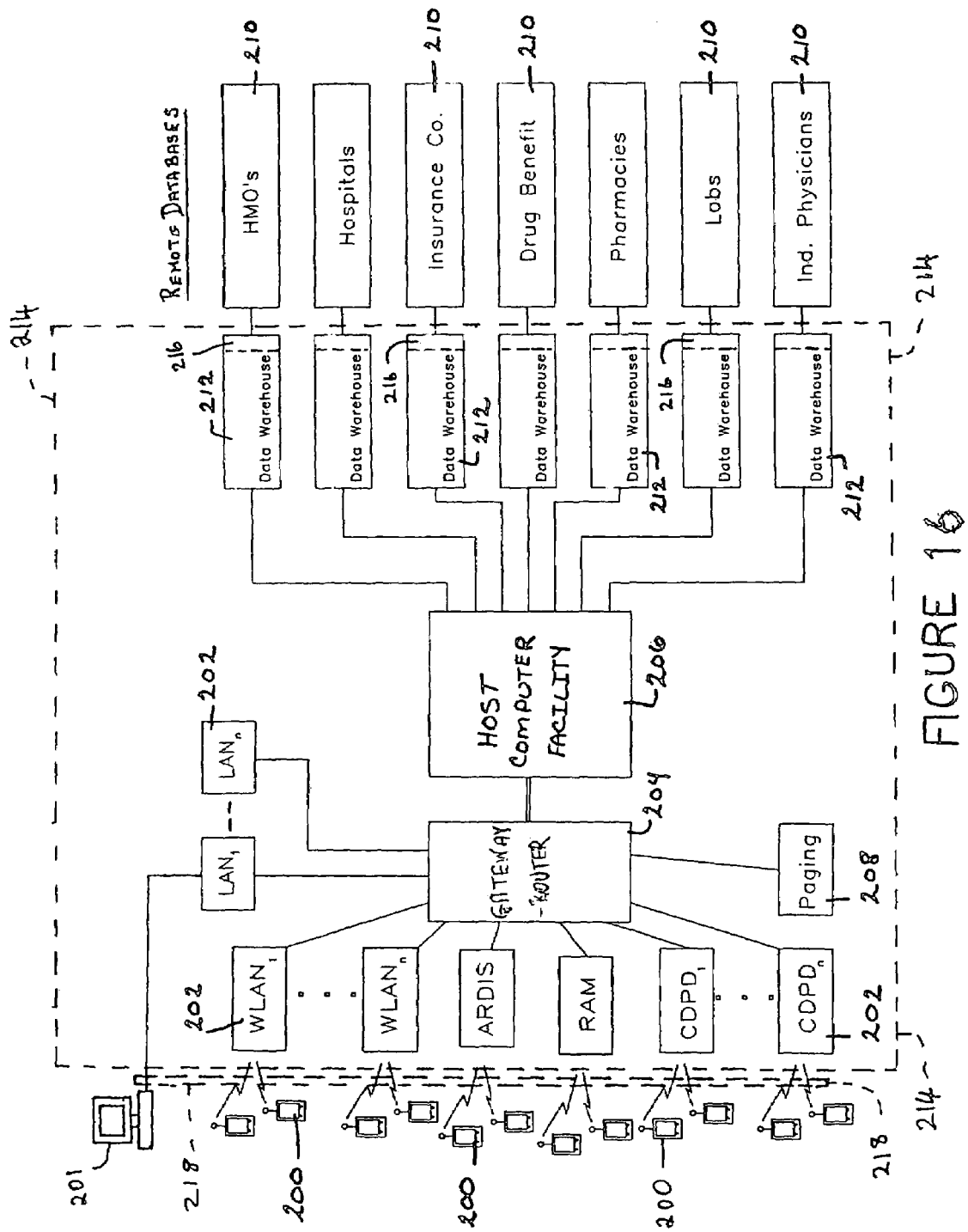
FIG. 16 is a schematic diagram of one way of connecting users of the prescription management system of FIGS. 1-14 with remote source databases across network to provide data and processing resources needed during operation of the prescription management system and useful inter alia for creation of a virtual patient record.

Referring to FIG. 16, the lefthand side of the diagram shows an arrangement of services and devices that provide a downstream flow of data and communications resources to users of the prescription management, or other system described herein. The righthand side shows sources from which desired data and data elements may be drawn and pathways for those data to reach the user, the flow being marshaled by a centrally depicted host computer.

Shown schematically in FIG. 16, are a number of user interface devices 200 and a desktop computer 201 communicating via any of a variety of communication services 202, through a gateway-router 204 with a host computer facility 206. The drawing depicts schematically how a group or pool of users working with interface devices 200 or computers 201, running the prescription management software of this invention, can be serviced by host computer facility 206. Those skilled in the art will appreciate that the schematic layout shown in FIG. 16 is described in terms of its logical architecture and that the actual physical disposition of elements may be quite different.

In addition to coordinating system-related communications, especially retrieval of source data from remote databases, gateway-router 204 can manage supplementary services such for example as a paging service 208 or any other relevant desired function.

Interface devices 200 are depicted as small form factor, handheld devices, or PDA's, communicating wirelessly over a WAN, a proprietary wireless service, or a cellular digital packet data service, or the like. Desktop computer 201, which may be a portable, notebook or other higher form factor computer, connected to communications gateway-router 204 via a local area network labeled LAN.sub.1. which connection could equally well be via modem, infra-red, wireless or the like, depending upon the circumstances. Any suitable network may be used, depending upon the user's equipment and the location of desired resources. Wired or wireless, local or wide area networks, or mixed networks, are suitable.

Routing to the appropriate service and other communications technicalities are coordinated by communications gateway-router 204 which is networked or otherwise connected with host computer facility 206.

Other prescribers (or other professionals in different environments) may use different methods to communicate with host computer facility 206 using a two-way digital data communication system across a network.

Still other users may be supported by other host computer facilities communicating in their turn with host computer facility 206 using appropriate network services and providing communication links or pathways between such other users and physician users supported by host computer facility 206. Such organizations employing one or more each of both users and host computer facilities are intended by references herein to "network" or the "network".

Communication services 202 can be any service providing effective two-way data transfer between users 200 and host computer facility 206. As labeled, some possible communication services 202 are wired local area networks "LAN.sub.1 . . . LAN.sub.n", wireless local area networks "WLAN.sub.1 . . . WLAN.sub.n" and proprietary radio frequency packet data networks, such as ARDIS and RAM (trademarks of their respective proprietors), cellular digital packet data networks "CDPD.sub.1 . . . CDPD.sub.n" and so on.

Not shown is a wire telephone connection between a user device 200 and communications gateway-router 204. This is of course a possible embodiment of the invention and it is also, to be understood, local area networks LAN.sub.n, could comprise a single desktop computer or a facility-based networked system of multiple desktop, or other computers.

Communications gateway-router 204 manages communications through these various media services and provides consistent interfaces to users at devices 200 and to host computer facility 206, regardless of which communication service 202 is used.

As referenced hereinabove, host computer facility 206 can comprise a client-server system in which a file server or database management server, or cluster of such servers, manage data storage and traffic functions, providing high volume data availability to multiple intelligent clients linked, typically over a local area network, to the server or servers.

Exchanging data, programs and processing services across this system, user interface devices 200 and host computer facility 206 support applications such as the prescription management system of the invention, E-Mail services and any other desired applications, for example patient encounter management programs, diagnostic procedure management programs, and the like, in an analogous manner to conventional client-server supported operation of such applications.

Host computer facility 206 provides intelligent network services to user devices 200 and 201 and may support ancillary services, especially for example, as described hereinbefore, patient-directed data access control software. Prescriber-directed data access control software or organization-directed data access control software could also run in an application separated from the prescription management system, but is preferably integrated therewith as a component of a user initialization routine.

Conveniently, patient interface components of the patient-directed data access control software are run at separate stations from the point-of-care locations used by prescribers and are located, for example, in administrative or reception areas of health care facilities or managed care organizations. Here, data access rights may be read off a patient's data access control card, and such cards may be issued, under control of software supplied by, and in communication with host computer facility 206.

The level of software and data resident on interfaces devices 200 can be varied according to their physical capabilities and user or system administrator preferences. At a minimum, and for device redundancy, interface devices 200 need have resident neither files nor software, beyond what is supplied with the device off the shelf.

So long as the user interface device has an operating system and is communications-equipped, they may establish communication with host computer facility 206, using a separately supplied electronic address for that facility and may upload necessary program components and data files, including such personalized user profiles as have been established by the user's prior experience with the system and which have been stored at the host computer facility 206, are called from a remote host computer facility supporting other users.

Neither such program components, nor data, need be stored on the interface device 200 but, where the device 200 has adequate storage capacity, it will be more convenient and faster-loading for a user to maintain configuration and user profile files, along with limited amounts of relevant drug, and possibly patient data, on the user's local interface device 200. Preferably, however basic system access software is required to be installed on the user device before system resources can be accessed. Such basic system access software can be activatable after reported loss or theft to disable system access capabilities and to render any stored proprietary data inaccessible to unauthorized users.

Host Computer Facility

Host computer facility 206 provides full software support for user interface devices 200 and maintains complete program files for the prescription management system along with e-mail services and any other non-personal applications that may be needed by users of devices 200 beyond the basic operating systems and utilities, and the like, with which the devices are originally equipped.

Host computer facility 206 maintains databases of patient information for patients encountered or whose records have previously been viewed by users of devices 200 in response to calls sent via host computer facility 206, (and logged by it for audit purposes) but, in keeping with the preferred practice of the present invention, host computer facility 206 does not maintain patient records in permanent storage. It could however be used to maintain patient record components that are source components to users of devices 200 for which this particular host facility 206 is, at it were, their "home" facility.

Important functions maintained by the host computer facility 206 are information locator databases and advanced directory and routing services, including the following:

i) a user device and system registry enabling communications to be routed to the target user;

ii) a patient information directory service enabling access the system to access remote databases to retrieve patient record components for compilation of virtual patient records as described above;

iii) archiving of transaction logs and records, and of audit logs;

iv) patient drug formularies and formulary guidelines or locators to access same;

v) libraries of alerts and other system displayed messages; and vi) access control software and related data files for patients, care providers and organizations.

Drug and condition lists and some drug information are also maintained on the host computer facility 206, but these are preferably either synchronized or refreshed at intervals (e.g. overnight) from source databases of such drug information. More detailed drug information (e.g. U.S. Pharmacopeia information) can be retrieved from remote databases by host computer facility 206. Host computer facility 206 also maintains directory services for accessing such drug related information, formularies, guidelines alert messages and the like and updates this data remotely from source databases maintained by the proprietors of the information.

Also in addition, host computer facility 206 can off-load data-processing functions from interface devices 200, or conduct such functions in background to provide support for the relatively limited processing capabilities of devices 200.

A further important function of host computer facility 206 is to retrieve multiple elements of a single patient record from multiple heterogenous remote databases and to deliver them to users for assembly into a virtual patient record by an interface device 200 or 201, in response to the user's call for that record.

Host facility 206 can reach out nationally, or internationally, for example across the INTERNET (trademark) to multiple remote databases such as remote databases 210 shown on the right hand side of FIG. 16, to provide to users of interface devices 200 data resources beyond (and potentially more current than) those available from direct storage in the device or at the host facility.

Communications

Communication between host computer facility 206 and remote databases 210 will usually be via wire lines such as telephone, or local or wide area network communication via copper line, or optical fiber, or any other suitable communication medium. Clearly, host computer facility 206 can access any remote third party database with which appropriate arrangements have been made, or can be made on line, and some possible source databases for patient records components are labeled as "HMO's, Hospitals Insurance, Drug Benefit Cos, Pharmacies, Labs and Independent Physicians". Drug information may be additionally sourced from pharmaceutical companies' research centers, reference libraries, or publishers and the like.

One or more pools of users of devices 200 and computers 201 constitute a valuable professional audience and the system provides a valuable means enabling such third party database proprietors to become data publishers and electronically publish or post their databases or on the network to reach that audience.

Using recognizable common record element identifiers, for example patient identification numbers or drug identifiers, host computer facility 206 forages across available networks for similarly identified record elements to retrieve. Employing its information directory services as locators, host computer facility can retrieve a variety of data including patient-specific data, application-specific data (users preferences and the like), organization-specific data (formulary guidelines, for example) and general drug or prescribing data, e.g. from MEDLINE.

To assist with compatibility problems with the legacy systems operating at remote databases 210 and to avoid heavy volumes of user calls, via the systems of the present invention, interfering with or slowing down the daily operations at the proprietary facilities supporting the remote data bases 210, this embodiment of the invention provides, at each of a limited number of remote databases 210 known to be a significant source of patient record elements, a dedicated data warehouse 212. Data warehouses 212 can be real or functional, depicting either actual physical embodiments of system-dedicated services located at the facilities of remote databases 210, or logical functions executed at the host computer facility 206.

Data warehouses 212, host computer facility 206, communications router-gateway 204 and communications services 204 are components of a conceptual integrating network 214 which brings users of devices 200 and 201 transparent access together with the resources available at remote databases 210, and preferably gives those users a seamless appearance, as though data stored piecemeal at multiple remote databases 212 were directly available from a single file across a local area network.

To facilitate connection with heterogenous databases, and to give their proprietors fluent access across the network, it is preferred that the system provides uniform application programming interfaces, remote API's 216 for use by third party developers. Compatible user API's 218 on the downstream side provide similar standardized connectivity with user devices 200 and 201.

Integrating network 214 and API's 216 and 218 permit easy system integration, allow third parties to develop end-to-end communications solutions with standardized third party communication across the network and a data "firewall" for security.

Data Warehouses 212

Each data warehouse 212 maintains replicated copies of relevant data sets obtained by read-only access of remote databases 210, which data sets are maintained synchronously with updated source data at remote databases 210, or are periodically refreshed therefrom, preferably at frequent intervals. Data warehouses 212 can also provide search and retrieval facilities and, in particular, provide protocol interchange and reformatting capabilities to reformat or otherwise standardize data and communications across network 214, for any application to use. Preferably, to facilitate compliance with the desired auditability of the transactions and data accesses of preferred embodiments of the invention, data warehouses 212 screen data incoming from associated data warehouses 210 for date-stamping, and preferably, also time-stamping, of individual received data or record elements, and reject those that lack such stamps. Preferably also, the date stamp indicates origination, creation or updating of the data element, rather than being merely a date of entry of the data element into data warehouse 212.

Source data generated by point-of-care or other transactions at user interface devices 200 or computers 201, can be directly posted to remote databases 210 across network 214 which bears two-way traffic. As will be apparent from the disclosure herein, remote databases also include data from other places, for example pharmacies, laboratories and testing facilities.

Communications gateway-router 204 also maintains a physician-device directory providing routing or access information needed to establish communication protocols with each individual physician. This device directory service can maintain an electronic address, a device identifier or device configuration, operating system information and user device communications protocols for each user device supported by the gateway-router. User ID's can be listed separately and in preferred embodiments are accompanied by a prioritized listing of one or more device addresses where the user may be accessed.

Other temporary or permanent update means are provided to enable a user to access the host computer facility from more than one device, preferably using an address that is device-independent.

It will be understood that an individual host computer facility 206 can serve one group of users that may, for example, be defined geographically and may number from, for example, as low as 10 or 20 users in the early days of establishment of the facility to hundreds and thousands as the facility matures. To service more users or to service users in other geographical areas, additional host computer facilities 206 can be established as centralized or regionally distributed hubs. Such additional host computer facilities 206 will, in all likelihood, access many of the same remote databases 210. Preferably, switching or rerouting means are provided to optimize data traffic loads between multiple host computer facilities 206.

It will also be understood that a national or international network can be created by establishing a sufficient number of host computer facilities 206 in strategic locations, each serving a local client base of, for example campus or regional users, with interface devices 200.

SUMMARY

The foregoing description has emphasized an approach to therapy prescribing which records an association between a therapeutic agent (drug) and a condition or problem targeted for resolution or amelioration by the prescribed therapeutic agent. Significant benefits derive from organizing known therapeutic agents according to conditions for which they are known to be effective, and emphasis has been placed herein on a drug selection and specification which begins with selection of a problem or condition to be treated, because this is be an appealing and beneficial approach in many circumstances. Frequently however, the physician may know exactly what drug they wish to prescribe, in which case they can proceed to a direct drug entry screen, and then specify the condition targeted by the prescribed treatment.

While emphasis has also been placed in the principle examples on the prescription of drugs, it will be appreciated that the invention can be beneficially applied to the specification of other therapies and technical remedies for example to the specification of surgical procedures, physical therapies and diagnostic testing.

Preferred embodiments of the invention include quick and easy routines for directly posting a drug to a prescription, without prior condition selection, such routines preferably being by-passed. In order to gain the subsequent historical review and outcome study benefits described herein, it is preferred to provide for inclusion of a treatment objective of the prescribed drug in the prescription record before completion of the prescription. The treatment objective can be rapidly selected from a system-supplied list of a patient's existing or historical conditions, or through powerful system-aided selection of a new condition. While a default patient condition or problem may be suggested by the system for a particular prescribed drug, it is preferred that such default be actively confirmed by the prescribing user before being accepted by the system.

To accommodate direct prescribing by drug name, Drug field 88 of the prescription creation screen of FIG. 3, can open a personalized or customized user-activatable drug list, or proceed to comprehensive system drug lists to enable rapid specification of familiar or unfamiliar drugs prior to condition selection. Drug dosage selection then proceeds as described above. Before leaving prescribing zone 44 of the prescription creation screen 39 the system can require an appropriate entry to be made in condition field 86.

Other preferred embodiments enable the patient, the prescribing physician and the relevant organization to control the flow of their own data by predetermining access rights to that data. Every transaction can be stamped with a patient identifier, a prescriber identifier and, if appropriate, an organization identifier, as well as with the date and time of day.

Emphasis on preferred, historical or customized short lists of drugs and conditions enables an attractive working environment to be provided even on relatively low power PDA's. Short list data may be maintained on the user device providing rapid responses in the user's most common prescribing situations. Less common situations entail calls to the host computer facility, in which circumstances delays of a few seconds while data is retrieved from the network are quite acceptable.

System Requirements

User software components of a currently preferred embodiment of prescription management system described herein are designed to run under an operating system that preferably supports a full or modified version of MS-DOS® (trademark, Microsoft Corporation) WINDOWS™ (Microsoft Corporation) or other systems with user-friendly graphical interfaces, for example Apple Computer Co.'s MACINTOSH (trademark) or NEWTON (trademark) operating systems and General Magic's MAGIC CAP operating system. Other graphical environments can be used or are being developed and other embodiments of the invention may be suitably modified to optimize the application to take advantage of the unique characteristics of each such operating system environment.

The programming language used to write system software depends upon the environment of the various system components. In their present stage of development, some handheld PDA's require applications to be written with the tools provided by their respective operating systems such as NEWTON or MAGIC CAP (trademarks). For other devices such as those supporting Microsoft's WINDOWS (trademark) operating system, including some PDA's, a range of languages can be used including for example, popular programming languages such as Microsoft Corporation's "C" or Borland International's "C++". For Apple Computer's MACINTOSH (TRADEMARK)-based systems, languages such as THINK (TRADEMARK) are appropriate.

The system is particularly advantageous when implemented on any of a variety of portable computer stations especially handheld units such as personal digital assistants and other personal information communicators equipped with wireless communicators. A preferred embodiment for mobile professionals comprises such a handheld unit with two-way radio or infrared communication facilities. Some such devices are referenced in a "BUYER'S GUIDE: PERSONAL DIGITAL ASSISTANTS" PC WEEK Aug. 29, 1994, pages 89 and 94 the disclosure of which is hereby incorporated herein by reference thereto.

For compatibility with the currently rather limited performance specifications of such desirable handheld devices the prescription management system of the invention is preferably designed to minimize the storage and processing requirements placed on the user's terminal and to off-load storage and processing to host computer facilities. Thus, the system's support architecture aims to supply to the user terminal only essential data required for screen displays and other user functions, on an as-needed basis, while the network stores applications and data files, for example at the host computer facility.

Modified Embodiments of the Invention

While the invention has been described with a reference to a particularly valuable embodiment of a prescription management system, it will be understood by those skilled in the art that alternative embodiments of the invention can bring valuable benefits in their respective fields where informed choice is desirable and can be facilitated by interactive computer-assisted decision-making, especially in situations where decision-relevant data is or can be drawn from multiple heterogenous remote databases.

Some such possible applications of the invention are to the specification of laboratory tests and also in the veterinary field, and to non-pharmaceutical environments where benefits such as valuable historical records and follow-up studies, as well as quality control improvements, can be obtained from coupling diagnostic conclusions with specified problem solutions.

Thus, according to one such a modified embodiment of the invention, laboratory test information can be presented to a prescribing professional by first listing patient conditions which the professional wishes to explore more fully by specifying one or more specific laboratory tests, by reporting the laboratory result and suggesting further testing for differential diagnostics. The system then provides a selection of laboratory tests known to be useful in evaluating the relevant condition, that selection and organization of laboratory tests being made in a manner similar to that described for therapeutic drugs in the preferred embodiments herein, and moves on to create, select and order appropriate cost-controllable diagnostic testing, in a comparable manner to that described herein for creating a prescription.

For example, an analogous diagnostic application may provide cost-effective routes to rule in or rule out specific diagnoses. The specificity and sensitivity of individual procedures can be translated into positive predictive values and negative predictive values. By applying decision theory and analyzing probable outcomes of procedures or combinations of procedures in the light of the patient's bio-characteristics and known conditions, diagnostic protocols can be worked up and maintained with current recommendations. Evaluation of the patient's history can enable pretest probabilities to be established and used to modulate the predictive value of one or more tests. Thus the patient's history can drive the selection and establishment of an optimal diagnostic test matrix for identifying a patient's condition or conditions with good specificity and confidence levels.

Test requirements relating to patient preparations, fasting for example, and sample collection can be system specified. By generating system-maintained identifiers (e.g. bar code labels) for attachment to samples at the point-of-care, a chain of evidence for rigorous sample accessioning can be begun.

Thus, a range of possible conditions can be evaluated in a differential diagnosis format designed to rule in or rule out a target condition, or conditions, depending upon the results of specified tests.

Extensions into the veterinary field will be apparent to those skilled in the art in that instead of the physician user referenced herein, reference to a veterinarian is appropriate, and the patient will be an animal such as a pet dog or cat or valuable livestock, such as a steer or breeding pig or a race horse or breeding stallion.

Again, although the invention has been described in its preferred embodiments with reference to a physician user it will be apparent that other medical professionals, especially those having prescribing authority, can benefit from applications of it.

In a more general sense, the invention provides a service professional with significant new benefits, especially during a service encounter with a customer or client, in selecting, specifying or providing technical remedies to consumer problems. For example, in specifying automotive replacement parts a service technician can benefit from an automotive service management system according to the invention in which a database of replacement parts is classified according to the service problem for which the parts might provide a remedy. Thus, for a customer with the problem of break squeal, the system may provide a list of parts, for example, brake pads, brake pins, brake shims or brake rotors, any of which may provide a remedy to the customers problem of brake squeal. Existing systems permit a service technician, having once identified the type of part they need, to obtain a number or part price and inventory on that part for the customer's specific model of car.

However, known systems do not permit the professional to query the system by customer problems, nor do they provide a summary of all facets of a solution to a problem leading to a summarized cost of treatment. In addition the inventive system can provide access to technical literature on relevant problems, for example an explanation of the factors causing brake squeal which can be printed out for customers. This is a rather simple example. More complex examples will be apparent to those skilled in the automotive and other arts, especially as this art develops, with sophisticated engine management and other microprocessor controlled systems raising new problems and new technical solutions being required. The inventive system can provide customer problem lists useful for outcome analysis to drive the development of better cars.

Of great value in the automotive and allied fields, equating a parts supplier, such as a factory or warehouse distributor with a plan benefit company is the ability to provide new product descriptive and price information or updates from multiple sources dynamically, in real time as transactions are created. Noting the desire of a benefits company to apply practical selection guidelines in an unobtrusive manner to the prescribing process, an equivalent technique can be used by car factories to help control warranty service decisions at their dealerships.

In another embodiment of the invention illustrating its generality, possible insurance vendors and coverage information may be classified according to customer problems so that, for example, an insurance agent may list different vendors and coverage providing specific technical remedies to a customers specific; problem, for example, a recent major automobile collision claim. The relevant novel supportive database could include information differentiating between parties at fault, collision damage, personal injury settlements and so on. In both these examples a problem history related either to the customer or to the customer's automobile can also be created.

It will be clear to those skilled in the art that use of the prescription management system described herein, employing carefully maintained databases of accurate, reliable prescribing data will produce high quality prescriptions free of many of the problems now plaguing prescription drug use. With confidence that a physician is prescribing appropriate, cost-effective drugs selected from user-personalized lists which link to comprehensive condition and drug lists including the latest available drugs, and that the prescribed drug has been reviewed for contraindications, patients benefit, oversight of the prescribing process by benefit companies and regulatory bodies can be reduced, and litigation resulting from prescribing errors will be reduced. Significant improvements in the quality of care, substantial savings and the elimination of waste can accrue to a national or regional healthcare system from widespread deployment of the inventive prescription management system described herein.

Physical Embodiment of System Software

The foregoing specification, read with the accompanying drawings provides an extensive disclosure of, inter alia, various embodiments of systems and software facilitating professionals to select or specify technical products to solve practical problems, and also to create, or assist the professional to create, new products which will assist the professional or their client in achieving desired problem-solving goals.

It will be understood that the systems and software referenced herein include, either explicitly, or implicitly, software implemented on computers or other appropriate hardware, including user devices such as the personal digital assistants described herein, and such other intelligent data processing devices having a processor, data storage means and the ability to support an operating system, with or without user interfaces (for example, file servers), as may be useful in achieving the objectives of this invention.

Software components and applications embodying the invention can be distributed in electronic bit storage on magnetic, optical, bubble or other media, optionally in transportable form to be interactive with an electronic reading device, for example on computer or optical diskettes, or may be distributed over wired or wireless networks for storage by the recipient on such media.

Preferred embodiments of the invention provide such media-stored software in a commercial package accompanied by instructions in printed book or booklet form, for deployment of the software on particular embodiments of general purpose computer to cause same to operate as a special purpose computer, in accordance with the objectives of the invention. License agreements, and registration means for updating may also be included. Alternatively, the instructions may also be provided as data files.

It will further be appreciated that such media-stored software constitutes an electronic customizing machine which can interact with a magnetically or optically cooperative computer-based input device enabling the computer to be customized as a special purpose computer, according to the contents of the software. To cause a computer to operate in such customized, special-purpose mode, the software of the invention can be installed by a user, or other, and will usually interact efficiently with the device on which it is resident to provide the desire special-purpose qualities, only after selection of configuration parameters. When so configured, the special-purpose computer device has enhanced value, especially to the professional users for whom it is intended.

While some illustrative embodiments of the invention have been described above, it is, of course, understood that various modifications will be apparent to those of ordinary skill in the art. Such modifications are within the spirit and scope of the invention, which is limited and defined only by the appended claims.

Thus, while certain aspects of the invention have been disclosed as embodied in connection with a prescription management system, it will be apparent that they have broader application in other systems or environments. Some of these aspects are: dynamic assembly of records from source record elements retrieved across a network from heterogenous remote databases; requirements for those elements to be time- and date-stamped for retrospective recreation of records from archival logs; physician-centric drug formularies; data-access control systems and software; the novel directory services described herein and associated online point-to-point e-mail and data retrieval systems; data retrieval networks with API-enabled end-to-end transparency; novel outcome studies, monitoring and alerting procedures, studies and related products; novel scheduled dosage drug packs and dispensing devices, and so on.

The invention claimed is:

1. A method of compiling a patient record at a location, comprising the steps of:
   a. interrogating databases located remotely from said location;
   b. selecting a database expected to contain information about a patient based on a patient's relationship with the provider of each database, said database selected from one or more of a group consisting of (a) a Health Maintenance Organization, (b) an insurance company, (c) a drug benefit plan, (d) a pharmacy run by a different organization than the organization running the user computer, (e) a laboratory, and (f) a physician practice; and
   b. assembling said patient information into a chronologically current version of said patient's medical history;
   c. outputting said assembled patient information.

2. A point-of-care prescription management system for selecting and dispensing an electronically generated drug prescription comprising:
   a host computer, said computer configured to perform the steps of:
   1. interrogating databases located remotely from said location;
   2. selecting a database expected to contain information about a patient based on a patient's relationship with the provider of each database, said database selected from one or more of a group consisting of (a) a Health Maintenance Organization, (b) an insurance company, (c) a drug benefit plan, (d) a pharmacy run by a different organization than the organization running the user computer, (e) a laboratory, and (f) a physician practice; and
   3. assembling patient information into a chronologically current version of said patient's medical history wherein said host computer is operatively associated with:
   a) at least one computer-readable unique patient identifier, each of said patient identifiers being logically linked to at least one database of patient information;
   b) at least one computer-readable patient condition identifier, each of said patient condition identifiers being logically linked to at least one database of medical condition information;
   c) at least one computer-readable prescribable drug identifier, each of said prescribable drug identifiers being logically linked to at least one database of drug information, and
   d) at least one computer-readable drug benefit provider identifier, each of said drug benefit provider identifiers being logically linked to at least one database of drug benefit provider information;

at least one user-interface device logically connected to said host computer, enabling dialogue between said host computer and a drug prescriber;

wherein said patient identifier is logically associated with at least one patient condition identifier and one drug benefit provider identifier, and each patient condition identifier is associated with at least one drug identifier, allowing said drug prescriber to prepare, capture, and transmit an electronic prescription to a drug fulfillment provider.

* * * * *